United States Patent
Beliaev et al.

(10) Patent No.: US 10,030,003 B2
(45) Date of Patent: Jul. 24, 2018

(54) SYNTHESIS OF ISOFLAVANES AND INTERMEDIATES THEREOF

(71) Applicant: System Biologie AG, Wollerau (CH)

(72) Inventors: Nikolai Beliaev, Ekaterinburg (RU); Yuri Shafran, Ekaterinburg (RU)

(73) Assignee: System Biologie AG, Wollerau (CH)

( * ) Notice: Subject to any disclaimer, the term of this patent is extended or adjusted under 35 U.S.C. 154(b) by 0 days.

(21) Appl. No.: 15/507,371

(22) PCT Filed: Sep. 9, 2015

(86) PCT No.: PCT/EP2015/070544
§ 371 (c)(1),
(2) Date: Feb. 28, 2017

(87) PCT Pub. No.: WO2016/038061
PCT Pub. Date: Mar. 17, 2016

(65) Prior Publication Data
US 2017/0283389 A1    Oct. 5, 2017

(30) Foreign Application Priority Data

Sep. 10, 2014   (EP) .................................... 14184240

(51) Int. Cl.
C07D 311/58   (2006.01)
C07D 311/38   (2006.01)
C07D 311/68   (2006.01)
C07D 405/12   (2006.01)

(52) U.S. Cl.
CPC .......... *C07D 311/58* (2013.01); *C07D 311/38* (2013.01); *C07D 311/68* (2013.01); *C07D 405/12* (2013.01)

(58) Field of Classification Search
CPC .................................................. C07D 311/58
See application file for complete search history.

(56) References Cited

U.S. PATENT DOCUMENTS

2007/0149788 A1   6/2007   Hyatt

FOREIGN PATENT DOCUMENTS

| EP | 1025850 A1 | 8/2000 |
|----|-----------|--------|
| WO | WO2004/039793 A1 | 5/2004 |
| WO | WO2007/016423 A2 | 2/2007 |
| WO | WO2010/018199 A1 | 2/2010 |

OTHER PUBLICATIONS

Amari et al., "Synthesis, pharmacological evaluation, and structure-activity relationships of benzopyran derivatives with potent SERM activity," Bioorganic & Medicinal Chemistry, vol. 12, pp. 3763-3782 (2004).

Badia et al., "A valuable route to benzopyrane[4,3-c]isoquinolines," Tetrahedron, vol. 54, pp. 233-242 (1998).

Heemstra et al., "Total Synthesis of (S)-Equol," Organic Letters, vol. 8, pp. 5441-5443 (2006).

Muthyala et al., "Equol, a natural estrogenic metabolite from soy isoflavones: convenient preparation and resolution of R- and S-equols and their differing binding and biological activity through estrogen receptors alpha and beta," Bioorganic & Medicinal Chemistry, vol. 12, pp. 1559-1567 (2004).

(Continued)

*Primary Examiner* — Paul V Ward
(74) *Attorney, Agent, or Firm* — Sonapat LLC

(57) ABSTRACT

Subject of the invention is a method for enantioselective production of an isoflavane from an isoflavone, comprising the steps: (a) selectively reducing the isoflavone, such that the 4-keto group of the isoflavone is converted to a 4-hydroxy group, and the 2,3-double bond of the isoflavone is converted to a 2,3-single bond, thereby obtaining a 4-hydroxy intermediate, and (b) reacting the 4-hydroxy intermediate with a chiral reagent, such that a chiral group is covalently attached to the C4-position of the 4-hydroxy intermediate, thereby obtaining a chiral intermediate. The invention also relates to intermediates of formulae (IV), (V), (VI) and (VII) obtainable in the inventive process.

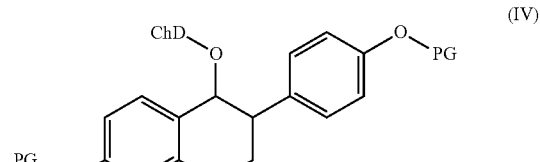

(IV)

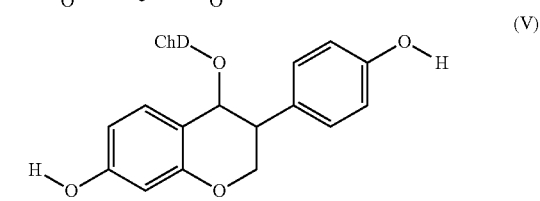

(V)

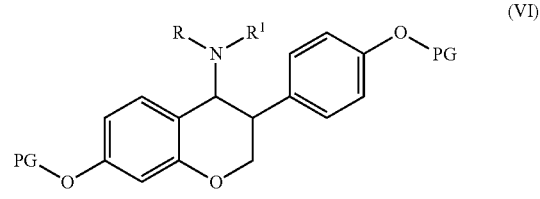

(VI)

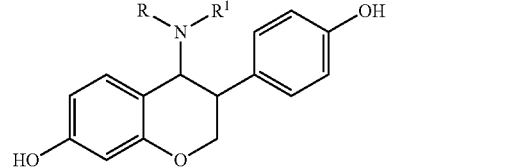

(VII)

20 Claims, No Drawings

(56) References Cited

OTHER PUBLICATIONS

Pihlaja et al., "Experimental and DFT 1H NMR Study of Conformational Equilibria in trans-4',7'-Dihydroxyisoflavan-4-ol and trans-Isoflavan-4-ol," J. Org. Chem., vol. 68, pp. 6864-6869 (2003).

Wahala et al., "The Synthesis, Structure, and Anticancer Activity of cis- and trans-4',7'-Dihydroxyisoflavan-4-ols," J. Org. Chem., vol. 62, pp. 7690-7693 (1997).

Yamaguchi et al., "Synthesis of trans-Isoflavan-4-ols," Bulletin of the Chemical Society of Japan, vol. 41, pp. 2073-2077 (1968).

SYNTHESIS OF ISOFLAVANES AND INTERMEDIATES THEREOF

BACKGROUND OF THE INVENTION

The subject of the invention is a method for the production of enantiomeric isoflavanes from isoflavones, and especially for producing R- or S-equol from daidzein. The method is characterized by a first reduction step and covalent attachment of a chiral compound, thereby obtaining a chiral intermediate.

Isoflavones, also referred to as isoflavonoids, are a class of organic compounds which often occur naturally. Isoflavones are compounds from plants, which, amongst others, play a role in the plants' defense against pathogens. Many isoflavones act as phytoestrogens in mammals. Some are antioxidants because of their ability to trap singlet oxygen. Some well-known isoflavones are daidzein, found as a glucoside of daidzin in soy flour, genistein from soy beans and red clover, prunetin from the bark of plum trees, biochanin A from chickpeas and clover, orobol, santal from sandle wood, red wood and other woods and pratensein from fresh red clover. Some isoflavones, in particular soy isoflavones, when studied in populations eating soy protein, have indicated that there is a lower incidence of breast cancer and other common cancers because of its role in influencing sex hormone metabolism and biological activity through intracellular enzymes, protein synthesis, growth factor actions, malignant cell proliferations, differentiation and angiogenesis. The isoflavone daidzein [4',7-dihydroxyisoflavone; 7-hydroxy-3-(4-hydroxyphenyl)-4H-1-benzopyran-4-one] is found in soy. It is a part of many foods and dietary supplements. It is easily available in relatively large amounts from soy.

Isoflavanes are synthesized in physiological pathways from isoflavones by selective reduction of the basic structure. The isoflavane equol [4',7-dihydroxyisoflavane; 3-(4-hydroxyphenyl)-7-chromanol] is produced in the intestinal flora after consumption of daidzein. The reaction is thought to be mediated by bacteria. Equol is thus a part of the group of secondary plant metabolites. After consumption of food which is rich in daidzein, equol is detectable in blood and urine. Equol has a mild estrogenic activity (0.1% of the activity of steroid-estrogens) and can bind to the estrogen receptors ERα and ERβ. Only about a third (Caucasian population) up to half (Japanese population) of humans can produce equol from daidzein. In humans who are capable of producing equol ("equol producers"), the cholesterol reducing and anti-inflammatory effect of a soy-rich diet is more pronounced when compared to humans, which are not capable of producing equol. In contrast to daidzein, naturally formed equol is chiral due to an asymmetric C3 atom. Various physiological activities have been attributed to S-equol as well as to R-equol. For S-equol, anti-proliferative effects were demonstrated in studies, for instance with respect to tissue changes in the breast which may occur in females during menopause. Equol inhibits DHT production in males due to interactions with the 5α reductase. It is assumed that DHT is a cause in the forming of prostate cancer in males.

The advantageous effects of isoflavanes and phytoestrogens such as equol are usually observed, if the compounds are consumed over an extended time period in significant amounts. Since the equol precursor daidzein is found in comparatively large amounts in soy, equol could be administered as a dietary supplement (food supplement, nutritional supplement). It would thus be highly desirable that equol is available by a simple production method, in large amounts and at low costs. Since equol is produced from daidzein in the intestine, it cannot be isolated in significant amounts from plants or other natural products. Thus, it can only be obtained in significant amounts by artificial synthesis.

Various publications disclose microbiological methods for producing equol. In this respect, EP 1 025 850 discloses a composition in which equol is produced microbiologically from soy isoflavones. However, microbiological production processes have various disadvantages, because microorganisms tend to change and thus do not yield uniform products. The production process thus has to be supervised continually, also to avoid contaminations. Further, the microorganisms have to be eliminated and removed from the composition after the production is completed.

Thus, there have been many efforts for producing equol by means of organic synthesis. For example, Muthyala et al. (Bioorg. Med. Chem., 2004, 12, p 1559-1567) describe a method for the production of equol from daidzein, which comprises a reduction of the 2,3-double bond and the keto group in the presence of a palladium hydroxide-catalyst of formula $Pd(OH)_2$. A racemate is obtained, which is separated into R-equol and S-equol by chromatography (HPLC). However, separation of racemates is generally difficult at industrial scale and chiral media for chromatographic separation are rather expensive.

Heemstra et al. (Organic Letters, 2006, 8, p 5441-5443) disclose an asymmetric synthesis of the chromane-ring by means of Evans-alkylation and intramolecular etherification according to Buchwald.

Patent application WO 2007/016423 A2 discloses a method for producing equol, which comprises reducing the 2,3-double bond and the 4-keto group of a substrate, elimination of the 4-OH-group under formation of a 3,4-double bond, synthesis of a specific iridium-catalyst and subsequent enantioselective reduction of the 3,4-double bond with the iridium catalyst.

Published patent application WO 2010/018199 A1 discloses a multiple-step process for producing isoflavanes from isoflavones, in which the 4-keto group is reduced in a first step in an enantioselective manner to the 4-hydroxy compound, whilst the C2,C3-double bond is maintained. In further steps, a protective group is attached to the 4-hydroxy group and the C2,C3-double bond is reduced. The process avoids precious metals and separation of enantiomers.

There is an ongoing need for alternative or improved synthesis methods, which increase the enantiomeric yield and render the overall process simpler and more economical. The known methods for producing equol are still relatively complicated, require multiple steps, or special and expensive reagents, or the yield is not high. Some processes require complex chiral catalysts and precious metals and multiple process steps. Some methods yield a racemate and require final separation into enantiomers, which requires multiple process steps and is complicated, especially at industrial scale. A simple and cost-efficient production, which would allow supplying large parts of the population with an adequate daily dose, is presently not available. Thus, in spite of all attempts for providing efficient methods for producing equol, the market price for R- or S-equol is still extremely high, presently more than 200 EUR per mg. Thus, R- or S-equol is presently still not commercially available in amounts for meeting therapeutic demands. Other isoflavanes, which also may have beneficial properties, are also not available.

Problem Underlying the Invention

The problem underlying the present invention is to provide a simple and cost-efficient method for the production of chiral isoflavanes, especially R- or S-equol. The method shall be applicable for obtaining the isoflavane at high enantiomeric and total yield. The method shall only comprise few reaction steps, which shall be simple. The use of complicated chemicals, such as chiral metal catalysts, shall be avoided. The use of toxic chemicals, which are not acceptable in pharmaceutical preparations, and thus have to be removed carefully in subsequent steps, shall be avoided. For example, reactive metals, like ruthenium or iridium, shall be avoided. The method shall enable synthesis of various isoflavanes, equol and derivatives thereof in a simple and convenient manner. Overall, the method shall provide for economical production of large amounts of isoflavanes.

SUBJECT OF THE INVENTION

Surprisingly, the problem underlying the invention is solved by methods and compounds of claims 1 to 17. Further embodiments are outlined in the description.

Subject of the invention is a method for enantioselective production of an isoflavane from an isoflavone, comprising the steps:
 (a) selectively reducing the isoflavone, such that the 4-keto group of the isoflavone is converted into a 4-hydroxy group and the 2,3-double bond of the isoflavone is converted into a 2,3-single bond, thereby obtaining a 4-hydroxy intermediate, and
 (b) reacting the 4-hydroxy intermediate with a chiral reagent, such that a chiral group is covalently attached to the C4-position of the 4-hydroxy intermediate, thereby obtaining a chiral intermediate.

Isoflavones are characterized by the common basic structure of formula (I):

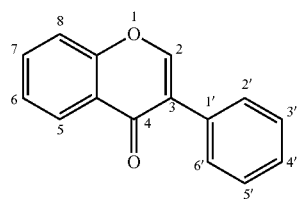

formula (I)

The basic structure does not comprise an asymmetric C-atom and thus the corresponding molecule is not chiral. The basic structure of the isoflavone may be substituted. Many naturally occurring isoflavones are substituted at the C5, C7, C3' and/or C4'-position. Typical substituents are hydroxy and/or methoxy groups. Preferably, the isoflavone is a derivative of formula (I), which is substituted at the C5, C7, C3' and/or C4'-position, preferably with a hydroxy and/or methoxy group.

Preferably, the isoflavone is a naturally occurring isoflavone. In a most preferred embodiment, the isoflavone is daidzein. However, it could also be another naturally occurring isoflavone, such as genistein, prunetin, biochanin A, orobol, santal or pratensein, or an artificial isoflavone, which comprises any other substituent attached to the basic structure, for example alkyl groups comprising 1 to 10 carbon atoms.

In preferred embodiments of the invention, the isoflavone has a structure of formula (Ia):

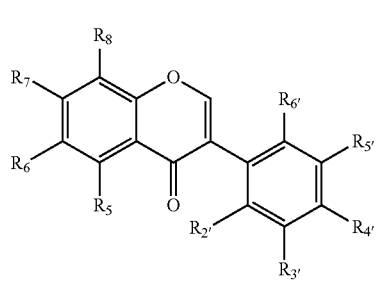

formula (Ia)

wherein $R_5$ to $R_8$ and $R_{2'}$ to $R_{6'}$ are selected independently from each other from H, hydroxy, $C_1$ to $C_{10}$ alkoxy, $C_1$ to $C_{10}$ alkyl, $C_1$ to $C_{10}$ alkenyl, $C_1$ to $C_{10}$ acyloxy, $C_1$ to $C_{10}$ aryloxy; halogen, preferably Cl, F or Br; or saturated and unsaturated cyclic groups containing 3 to 20 carbon atoms and optionally oxygen atoms, the cyclic groups being annelated to one or both phenyl rings. Preferably, at least 3 substituents in formula (Ia) are H and at least one substituent is hydroxy. More preferably, $R_5$ to $R_8$ and $R_{2'}$ to $R_{6'}$ are selected independently from each other from H, hydroxy, $C_1$ to $C_5$ alkoxy and $C_1$ to $C_5$ alkyl, whereby at least 4 substituents are H and at least one substituent is hydroxy.

Isoflavanes have a basic structure corresponding to isoflavones, but with a —$CH_2$— group at the C4-position and a C2-C3-single bond. The basic structure of the isoflavane is characterized by an asymmetric C3 atom, which imparts chirality to the isoflavane. The common basic structure is shown in formula (II).

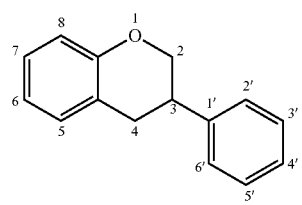

formula (II)

Preferably, the isoflavanes obtained in the inventive process are those corresponding to the isoflavones described above, such as those in formula (Ia). In other words, the isoflavone substrates used in the inventive method and isoflavanes obtained according to the process have the same substituents, but the basic structure differs at positions C2, C3 and C4 as shown in formula (I) and (II) above.

The method of the invention is enantioselective. This means, that an isoflavane is obtained, which is an enantiomer (the R- or S-form), or a mixture of both enantiomers in which one enantiomer (the R- or S-form) is enriched. The desired enantiomer is obtained in enantiomeric excess. Production of an enantiomer having 100% purity, although desirable, is theoretically achievable, but would require multiple subsequent purification steps.

In the inventive process, a chiral isoflavane is produced from an isoflavone, the basic structure of which is non-chiral. Typically, the isoflavone is non-chiral (unless it has a chiral substituent). A chiral center is introduced in the inventive process in step (b), when the chiral compound is covalently attached to the substrate. In the present application, the intermediate obtained in step (b) is referred to as "chiral intermediate", because the chiral substituent is essential for the subsequent and overall process. However, this shall not imply that the chiral intermediate has only one chiral carbon atom. The hydroxyl intermediate obtained in step (a) already comprised asymmetric C3 and C4 carbon atoms, which are preserved in the chiral intermediate.

In the preceding reduction step (a), a hydroxy intermediate is obtained which has two asymmetric C3 and C4 atoms. Preferably, the catalyst is non-chiral. In this case, there is typically no substantial enrichment of a certain stereoisomer. Whether the S- or R-form of the isoflavane is finally obtained, depends on the reagents and conditions of the following steps, especially on step (b) and the selection of the chiral reagent. In step (b), a mixture of stereoisomers can be obtained.

The isoflavane is preferably equol. In this embodiment, the isoflavone substrate is daidzein. Equol, as daidzein, has two hydroxy groups attached to the C7 and C4' of the basic structure. S-equol has the following formula (III).

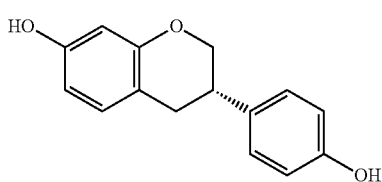

formula (III)

The inventive process may yield S-equol or R-equol, or a reaction product having an enantiomeric excess of S-equol or of R-equol.

The inventive process is specific. In the inventive process, the isoflavone basic structure, which is not explicitly reacted as outlined in the process steps, is maintained. Especially, the two phenyl rings and any substituents of the basic structure of the isoflavone are not affected, except for the reductions for obtaining the corresponding isoflavane, which are reduction of the keto group and C2,C3-double bond, and except for attachment or displacement of protective groups to hydroxy groups. In other words, the process yields the isoflavane precisely corresponding to the isoflavone starting compound. Nonetheless, the substituents, especially hydroxy groups, may be covalently modified with protective groups and/or such protective groups may be removed during the inventive process.

In a preferred embodiment of the invention, the method comprises a step (c) following step (b):
(c) reacting the chiral intermediate with an amine reagent, such that an amine group is covalently attached to the C4-position, whereas the chiral group is removed from the C4-position, thereby obtaining an amine intermediate.

The amine intermediate has two asymmetric carbon atoms at the C3- and C4-positions. Preferably, in step (c) the chiral intermediate is used from the preceding step (b). It is possible to use the direct reaction product from step (b). Alternatively, the chiral intermediate can be purified or enriched after step (b) by one or more intermediate steps, such as crystallization. The amine is covalently attached to the C4 carbon, preferably by a C—N single bond.

In a preferred embodiment of the invention, the method comprises a step (d) following step (c):

(d) reducing the amine intermediate at the C4-position to obtain a —CH$_2$— group at the C4-position.

In this reduction step, the amine group is detached from the C4-position. The chirality of the C4-carbon atom is lost. The only remaining asymmetric carbon atom is at the C3-position of the basic structure. The chirality of the C3-position is not affected. Therefore, the chiral intermediate from step (b) can be converted into the corresponding isoflavane. The reduction is selective. In other words, no other position of the amine intermediate is reduced, or at least not in a significant amount.

In a preferred embodiment, the isoflavanol used in the inventive process in step (b), in which the chiral reagent is reacted with the 4-hydroxy group, has protective groups covalently attached to the hydroxy groups except for the 4-hydroxy group. For example, when daidzein is used for producing equol, in step (a), a derivative of daidzein is used, which has the 4'- and 7-hydroxy groups protected. The protective groups can be introduced by known means at any stage before step (b) of the process. For example, they could be covalently attached to the isoflavone, or selectively to the 4-hydroxy intermediate, or to an intermediate having the C2-C3-double bond of the isoflavone already selectively reduced to a single bond.

In a preferred embodiment, the isoflavone used in the inventive process in step (a) has protective groups covalently attached to hydroxy groups. For example, when daidzein is used for producing equol, in step (a), a derivative of daidzein is used, which has the 4'- and 7-hydroxy groups protected.

In a preferred embodiment of the invention, the method comprises a step (a0) preceding step (a):
(a0) covalently attaching protective groups to the hydroxy groups of the isoflavone.

In an alternative embodiment, the method comprises a step (b0) preceding step (b):
(b0) covalently attaching protective groups to the hydroxy groups of the 4-hydroxy intermediate.

In this embodiment, the selective group could be introduced selectively such that the 4-hydroxy group does not react, or reacts less than the other hydroxy groups. However, typically a mixture of intermediate compounds with hydroxy groups attached to different positions is obtained, which has to be separated. Thus, the method is usually more complicated and less preferred. The 4-hydroxy intermediate could also be fully protected, followed by selective removal of the protective group at the 4-hydroxy group.

In an alternative embodiment, the method comprises a step (b0a) preceding step (b):
(b0a) covalently attaching protective groups to the hydroxy groups of a precursor of the 4-hydroxy intermediate, of which the C2,C3-double bond was already selectively reduced to a C2,C3-single bond.

In this embodiment, the protective groups are attached to an intermediate isoflavanone. Typically, the carbonyl group at the C4 position does not react with the protective reagent.

Preferably, at the end of the inventive process, or in a reaction step close to the end, the protective groups are removed to obtain the desired isoflavane. The protective groups may be removed in one of the process steps, or in a separate additional step. Alternatively, the final product may have the protective groups attached.

In a preferred embodiment, the protective groups are removed from the hydroxy groups during or after step (c) or (d). Thereby, the overall process is simplified. In case the protective groups are not cleaved off during step (c) or (d), they can be removed in a subsequent deprotection step (e).

Step (c) can be carried out directly with the reaction product of step (b). However, it is preferred that the method comprises an intermediate step (b1) after step (b) and before step (c):

(b1) separating diastereomers of the chiral intermediate, preferably by crystallization.

Preferably, step (b1) is carried out directly before step (c). In step (b1), a stereoisomer of the chiral intermediate, which is a diastereomer, is enriched or purified. It was found that in a crystallization step, a desired diastereomer can be enriched efficiently, because the reaction product of step (b) comprises diastereomers having different physical properties. The separation of such diastereomers having different physical properties, such as solubility, can be carried out by crystallization from non-chiral solvent, whereas separation of enantiomers by crystallization from non-chiral solvent is impossible. Further, it was found that the reaction product of step (b) does not comprise all four conceivable stereoisomers in equivalent amounts. Rather, some stereoisomers are enriched and the others are not significantly formed. When producing equol from daidzein, a mixture of two main stereoisomers was obtained as the chiral intermediate in step (b), which can efficiently be separated by crystallization.

In a preferred embodiment, step (b1) comprises the evaporation of the solvent, re-dissolving the reaction product in a crystallization solvent, and crystallization and/or extraction. The crystallization and/or can be repeated once or several times. Preferably, the solvent for crystallization is an alcohol, such as 2-propanol. After crystallization, the precipitate can be isolated and purified further, for example by filtering, washing with solvent and drying. The purified chiral intermediate thus obtained can be used in subsequent step (c).

In a preferred embodiment of the invention, the method comprises the steps:

(a0) optionally, covalently attaching protective groups to the hydroxy groups of the isoflavone, (a) selectively reducing the isoflavone, such that the 4-keto group of the isoflavone is converted to a 4-hydroxy group, and the 2,3-double bond of the isoflavone is converted into a 2,3-single bond, thereby obtaining a 4-hydroxy intermediate, (b) reacting the 4-hydroxy intermediate with a chiral reagent, such that a chiral group is covalently attached to the C4-position of the 4-hydroxy intermediate, thereby obtaining a chiral intermediate, (b1) separating stereoisomers of the chiral intermediate by crystallization, (c) reacting the chiral intermediate with an amine reagent, such that an amine group is covalently attached to the C4-position, whereas the chiral group is removed from the C4-position, thereby obtaining an amine intermediate, and (d) reducing the amine intermediate at the C4-position of to obtain a —$CH_2$— group at the C4-position, wherein during or after step (c) or (d), the protective groups are optionally removed from the hydroxy groups.

Preferably, reaction steps (a0) to (d) are carried out in consecutive order. Preferably, the overall synthesis consists of steps (a0) to (d). The "synthesis" in this respect is the chemical reaction, not including purification steps and other physical modifications. A preferred method of the invention for producing equol from daidzein is shown schematically in reaction scheme 1.

Scheme 1: Synthesis of equol from daidzein

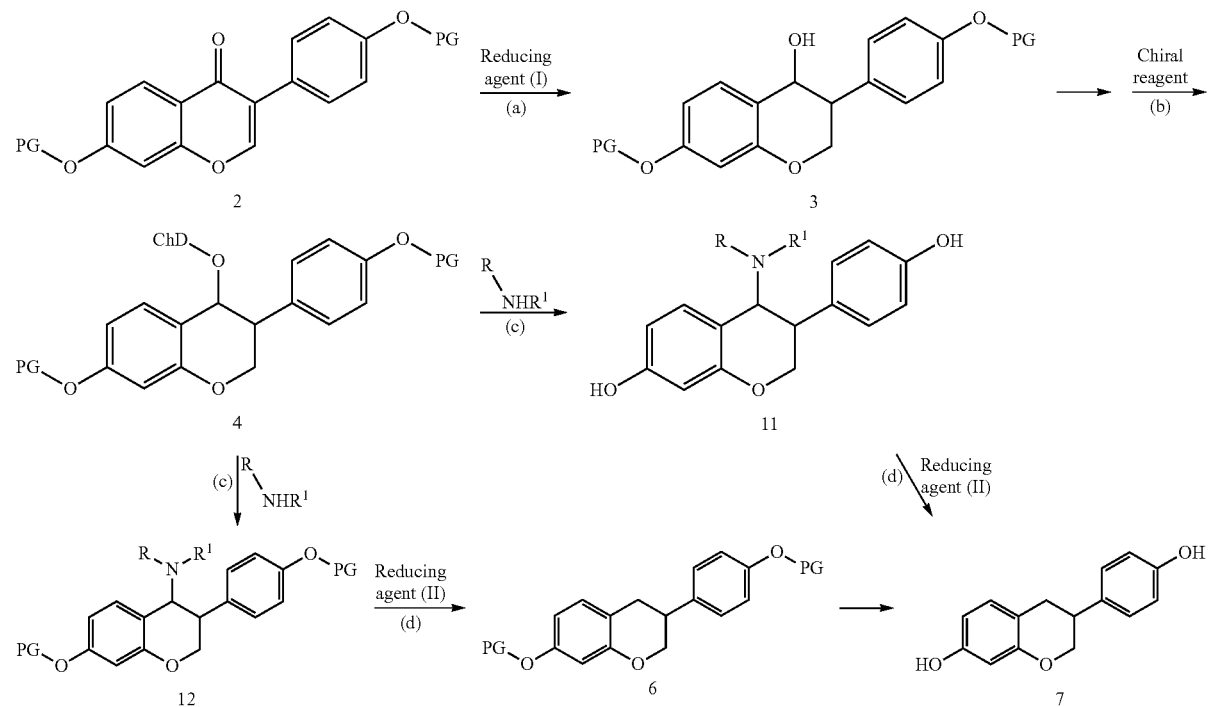

Abbreviations:
PG = protecting group, ChD = chiral group; $RNHR^1$ is the amine reagent In scheme 1, the starting compound is daidzein with protective groups attached to the 4'- and 7-hydroxy groups (compound 2). The protected daidzein 2 is reduced in step (a) to the hydroxy intermediate 3. In step (b), a chiral group is covalently attached to the C4-position to obtain chiral intermediate 4. Subsequently, diastereomers obtained in the reaction mixture can be separated by crystallization or extraction to obtain a purified chiral intermediate 4 having a desired stereochemical structure. In step (c), chiral intermediate 4 is converted into amine intermediate 11 or 12 with an amine reagent. Amine intermediate 11 can be reduced subsequently in step (d) to isoflavane 7. Amine intermediate 12 still has protective groups attached to the hydroxy groups. In step (d), selective reduction of the C4-position yields a —$CH_2$-group, thereby obtaining protected isoflavane 6 and/or deprotected isoflavane 7. Whether amine intermediate 11 or 12 is obtained depends mostly on the selection of the protecting group. However, both pathways are applicable for producing isoflavane 7. Overall, R- or S-equol 7 is obtained.

Reaction step (a) is a reduction. Preferably, a reducing agent is used in combination with a catalyst. It is not necessary and not preferred that this reduction is enantioselective. The 4-hydroxy intermediate has asymmetric C3- and C4-carbon atoms. When a simple, non-chiral reducing agent and/or catalyst is/are used, the 4-hydroxy intermediate is a racemic (non-chiral) mixture of two pairs of diastereomers. Preferably, the metal catalyst is selected from palladium/carbon, Raney nickel, platinum (IV) oxide and $Pd(OH)_2$, and/or the reducing reagent is selected from hydrogen, ammonium formate, formic acid and cyclohexene. In a preferred embodiment of the invention, the reduction in step (a) is carried out in the presence of a metal catalyst, preferably palladium/carbon in combination with hydrogen.

The use of hydrogen/palladium/carbon in reaction step (a) is especially preferred. With this catalyst and reducing agent, it is possible to reduce the 4-keto group selectively to the 4-hydroxy group, without subsequent further reduction to the 4-$CH_2$-group. Further, this catalyst system does not significantly affect other substituents or the basic structure of the isoflavone. Overall, the 4-hydroxy intermediate is obtainable at high yield.

Further, it was found that the yield of the 4-hydroxy intermediate can be increased when carrying out the reduction in step (a) with palladium/carbon/hydrogen at enhanced temperature. Preferably, the temperature is between 50° C. and 100° C., more preferably between 65° C. and 90° C., most preferably between 75° C. and 80° C. It was found that when carrying out the reaction at such an enhanced temperature with hydrogen/palladium/carbon, the yield of the 4-hydroxy intermediate can be more than 90%. Preferably, the amount of palladium in the solid catalyst is between 2 and 15 wt. %, more preferably between 3 and 8 wt. %. Very good results are obtained when using a palladium/carbon catalyst comprising about 5 wt. % palladium.

The reaction in step (a) could also be carried out in two steps. In a first step, a partial reduction is carried out to selectively reduce the 2,3-double bond to a single bond, whilst the 4-carbonyl group is maintained. Preferably, the first step is a hydrogenation with $H_2$ under mild conditions, for example with Pd/C catalyst. In the second step, the carbonyl group is reduced, preferably with sodium borohydride, to obtain the 4-hydroxy intermediate.

Preferably, the chiral reagent used in step (b) is an organic low molecular weight compound. It is highly preferred that it has only one asymmetric atom, preferably an asymmetric carbon atom. Preferably, the enantiomeric purity of the chiral reagent is high, for example at least 90% ee, at least 95% ee or at least 98% ee.

Preferably, the chiral group is bulky. Frequently, bulky substituents comprise branched alkyl moieties, aliphatic or aromatic rings and/or ring structures, wherein the ring structures may comprise one or more aliphatic, heteroaliphatic, aromatic or heteroaromatic rings or any combination thereof.

Preferably, the chiral reagent comprises 1 to 5 rings. In preferred embodiments, the rings are naphthalene, pyrrolidine, benzyl or hexyl and/or the ring structures are camphor or derivatives thereof. The chiral reagent may comprise a ring system having 2, 3 or 4 rings.

Preferably, the chiral group and/or chiral reagent comprise at least 8, especially 8 to 30, or 10 to 20 carbon atoms. The rings and/or chiral reagent may comprise 1 to 8 heteroatoms, such as O, N or S. The molecular weight of the chiral reagent could be between 100 and 600 Da, preferably between 150 and 300 Da.

In a preferred embodiment of the invention, the chiral reagent in step (b) comprises an acid group, which is preferably activated, and at least one ring. Preferably, the chiral reagent is an acid halogenide, preferably an acid chloride. Activation of organic acids is achieved by methods known in the art, for example with thionyl chloride. The organic ring may be an aromatic ring or aliphatic ring. The rings may be annelated.

In a preferred embodiment, the chiral reagent in step (b) has 8 to 30 carbon atoms, a chiral carbon atom, which is preferably a single chiral atom, optionally 1 to 8 heteroatoms, preferably selected from O, N, or S; and 1 to 5 rings, and preferably an activated acid group (for formation of an ester linkage to the isoflavane).

In a preferred embodiment, the chiral reagent in step (b) has a molecular weight between 100 and 600 Da, comprises an activated acid group and 1 to 5 rings. Preferably, this chiral reagent comprises a chiral carbon atom, which is preferably a single chiral atom, a total of 8 to 30 carbon atoms, and optionally 1 to 8 heteroatoms, such as O, N, or S.

In a preferred embodiment of the invention, the acid group is an activated carboxyl or sulfonyl group and/or the organic ring is, or is part of, at least one group selected from alkylnaphthyl, 1,4-benzodioxane, camphor, cyclohexyl, alkylbenzyl, tetrahydrofuran and pyrrolidine.

Preferred chiral reagents for use in step (b) are selected from S- or R-naproxen (2-(6-methoxy-2-naphthyl)propanoic acid; S- or R-enantiomer), (2S)-(acetyloxy)(phenyl) acetic acid or a proline derivative, such as N-p-tosyl-L-proline, N-(4-fluorophenyl)sulfonyl-L-proline, N-benzoyl-L-proline, N-(4-bromobenzyl)-L-proline or N-benzyl-L-proline, (R)-1,4-benzodioxane-2-carboxylic acid, (S)-1,4-benzodioxane-2-carboxylic acid, (1R)-(+)-camphanic acid, (1S)-(−)-camphanic acid, (1R)-(−)-10-camphorsulfonic acid, (1S)-(+)-10-camphorsulfonic acid, (1S)-(+)-10-camphorsulfonyl chloride, (1R)-(−)-10-camphorsulfonyl chloride, (1R)-(−)-menthyl chloroformate, (1S)-(+)-menthyl chloroformate, (−)-menthyloxyacetic acid, (+)-menthyloxyacetic acid, (R)-(−)-α-methoxyphenylacetic acid, (S)-(+)-α-methoxyphenylacetic acid, (R)-(+)-α-methoxy-α-trifluoromethylphenylacetic acid, (S)-(−)-α-methoxy-α-(trifluoromethyl)phenylacetic acid, (R)-(−)-5-oxo-2-tetrahydrofurancarboxylic acid, (S)-(+)-5-oxo-2-tetrahydrofurancarboxylic acid, (R)-(−)-2-phenylpropionic acid, (S)-(+)-2-phenylpropionic acid, L-pyroglutamic acid, (+)-O,O'-diacetyl-L-tartaric anhydride, or the corresponding other enantiomeric forms (R- or S-form) of any of these compounds, or a corresponding activated compound. All these compounds comprise at least one organic ring and an acid group. All these compounds are commercially available at enantiomeric purity of 97 to 100%, for example from the commercial supplier Sigma-Aldrich, US.

In a highly preferred embodiment, the chiral reagent is a proline derivative, especially a derivative having an aromatic group attached to the N of the pyrrolidine group, or a corresponding activated compound. Preferably, the proline derivative is selected from N-p-tosyl-L-proline, N-(4-fluorophenyl)sulfonyl-L-proline, N-benzoyl-L-proline, N-(4-bromobenzyl)-L-proline and N-benzyl-L-proline, or the other corresponding enantiomeric forms (R- or S-form) of any of these compounds or a corresponding activated compound. More preferably, the proline derivative is selected from N-p-tosyl-L-proline or N-(4-fluorophenyl)sulfonyl-L-proline. As shown in the working examples, R- or S-equol can be obtained at high yield from daidzein when using such proline derivatives as the chiral reagent.

In a highly preferred embodiment, the chiral reagent is S- or R-naproxen or a corresponding activated compound, preferably naproxen chloride. As shown in the working examples, R-equol can be obtained at high yield from daidzein when using S-naproxen as the chiral reagent. Likewise, S-equol can be obtained when using R-naproxen at the same yield. In another highly preferred embodiment, the chiral reagent is (2S)-(acetyloxy)(phenyl)acetic acid, or a corresponding other enantiomeric form, or a corresponding activated compound. This chiral agent is advantageous, because it is easily available from mandelic acid.

In a highly preferred embodiment, the chiral reagent is selected from (2S)-(acetyloxy)(phenyl)acetic acid, N-p-tosyl-L-proline, N-(4-fluorophenyl)sulfonyl-L-proline or naproxen or a corresponding activated compound.

Preferably, reaction step (b) is carried out with the activated chiral reagent, for example an activated analogue of any of the chiral reagents above, preferably an activated acid, preferably an acid chloride, such as carboxylic acid chloride or sulfonyl chloride. Preferably, the reaction is carried out in the presence of a base, preferably a weak base, preferably an amine base, such as pyridine. It was found that the reaction can be efficient, when simply reacting the 4-hydroxy intermediate with the activated chiral reagent in the presence of an amine base, such as pyridine. The chiral reagent could also be attached by the carbodiimide method, for example with HBTU or HCTU. In a preferred method, a chiral reagent which is a carbonyl chloride or sulfonyl chloride is reacted with 4',7'-diprotected tetrahydrodaidzein, preferably in the presence of pyridine.

The chiral group is covalently attached to the C4-position of the basic structure. The C4 carbon atom is chiral. The specific linkage of the chiral group to the C4 position is not decisive for the inventive process. The chiral group could be attached to the C4 carbon atom by an acyl, ether or ester bond. Typically, the C4 carbon is linked via the hydroxy group (which forms an ether or ester bond with the chiral group). The chiral intermediate may be any compound obtainable by reacting isoflavone substrates as described above, for example isoflavones of formula (I) or (Ia) above, by steps (a) and (b) as described above, which has the chiral group covalently attached to the chiral C4 atom.

Preferably, the chiral intermediate has a structure of formula (Ib):

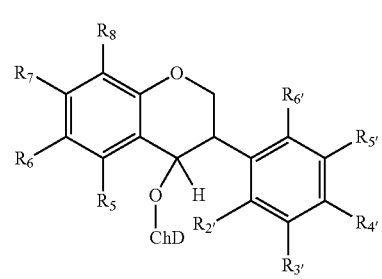

formula (Ib)

wherein ChD is the chiral group and the other residues are defined as for formula (Ia) above. Preferably, ChD is linked to the basic structure shown in formula (Ib) via an acyl group. Thus, the chiral group would be linked to the C4-atom by an ester bond.

As noted above, the specific structure of the chiral intermediate is not relevant for carrying out the inventive process, provided that the C4 carbon atom of the chiral intermediate obtained in step (b) of the process is chiral. Thus, the chiral intermediate, or at least a certain amount of chiral intermediate, may have another structure at the C4 atom as shown in formula (Ib). Such other chiral compounds could also be used for preparing isoflavanes from isoflavones in the inventive process. For example, the chiral group attached to the C4 carbon atom of the chiral intermediate could be attached whilst the C4-O bond of the 4-hydroxy intermediate is maintained. Especially, a chiral group could be attached by acylation, whereas the C4-hydroxy group is maintained. Then, the chiral intermediate would have asymmetric C3- and C4-carbon atoms and a hydroxy group attached to the C4 carbon. Thus, in a specific embodiment, the chiral intermediate may have an asymmetric C4-carbon atom, to which a hydroxy group and the chiral group, preferably via an acyl group, are attached. But as noted above, such theoretical details of the process are not relevant for carrying out the invention.

The chiral group imparts chirality to the chiral intermediate. This is used as a starting point for obtaining a corresponding R- or S-isoflavane later in the process. The chiral intermediate comprises asymmetric carbon atoms C3 and C4 of the basic structure, and further the predetermined chirality of the chiral group. In reaction step (b), in theory four different diastereomers could be expected (varying at the C3- and C4-positions). Surprisingly, it was found that less stereoisomers are obtained, and some prevail. For example, only 2 of the 4 stereoisomers are found, which are diastereomers. It is preferred that in step (b), one stereoisomer is obtained as the main product, which preferably amounts to at least 40%, more preferably at least 50% or at least 60% of all chiral intermediates obtained. Preferably, this enriched stereoisomer is converted into the desired isoflavane in the subsequent steps.

In a step (b1), diastereomers present in the chiral intermediate can be separated. Specifically, one of the diastereomers can be purified or enriched, preferably by crystallization. Thereby, a desired diastereomer is obtained at higher concentration. It was found that separation by crystallization of diastereomers of the chiral product of step (b) is efficient, because the reaction mixture usually does not comprises all conceivable diastereomers in significant amounts. The diastereomers formed can be separated due to their different physical properties, preferably by crystallization. The crystallization can be carried out relatively simply in a single step from alcohol, such as 2-propanol. Thereby, also other side products and impurities can be removed. Preferably, the yield of the desired specific stereoisomer in step (b1) is at least 75%, more preferably at least 90%, based on the sum of all chiral intermediates.

In reaction step (c), an amine intermediate is obtained. The amine group is covalently attached to the C4-position, whereas the chiral group is removed from the C4-position. In this reaction step, the chirality of the C3-position is preferably not changed, or at least not for a significant amount of the product.

In a preferred embodiment of the invention, the amine reagent in step (c) is a secondary amine, preferably a cyclic secondary amine having 5 to 20 carbon atoms or a secondary non-cyclic amine, preferably a dialkylamine, wherein each alkyl group has 1 to 20 carbon atoms. In a preferred embodiment of the invention, the amine reagent in step (c) is a cyclic amine, preferably having one ring. Besides the at least one NH group, the ring may comprise at least one other heteroatom or group, such as O or S. For cyclic amines, β-substituted derivatives could also be used, which are preferably β-substituted with an alkyl group having 1 to 10 carbon atoms.

Preferably, the amine reagent is an amine base. This means that it reacts as an amine base in the specific reaction of step (c). Preferably, the amine reagent is selected from morpholine, C-substituted morpholine, N-substituted piperazine, pyrrolidine, piperidine, dimethylamine and diethylamine. For example, the C-substitution or N-substitution could be with C1 to C5 alkyl.

Preferably, the amine reagent is a mild base, for example having a $pK_a$ value between 7.5 and 10.0 or between 8.0 and 9.0 (determined in water). It is especially preferred that the amine reagent in step (c) is morpholine. Morpholine is a mild base having a $pK_a$ value of 8.36.

Step (c) can be carried out simply by reacting the chiral intermediate with the amine reagent in a solvent. The chiral intermediate can be the direct reaction product of step (b), or a reaction product of step (b) which has been further purified, for example in separation step (b1). The solvent is preferably an inert solvent, such as dioxane. After the reaction, the amine intermediate can be purified by precipitation, filtering and optionally washing.

In a preferred embodiment of the invention, the reduction in step (d) is carried out in the presence of a metal catalyst and a reducing agent. Preferably, the metal catalyst is selected from palladium/carbon, Raney nickel, platinum (IV) oxide and $Pd(OH)_2$, and/or the reducing reagent is selected from hydrogen, ammonium formate, formic acid and cyclohexene. Preferably, the metal catalyst is preferably palladium/carbon or $Pd(OH)_2$/charcoal and the reducing agent is hydrogen.

Reduction step (d) is carried out by known methods in an appropriate solvent, such as ethanol. In a preferred embodiment, not only the amine group is detached from the C4-position, but also the protective groups are removed. Alternatively, the reduction can be carried out such that the amine group is removed, and the protective groups could be removed subsequently. Removal of some protective groups can be controlled by adjusting the catalyst activity as known in the art, for example by adjusting the temperature or the ratio palladium/carbon. For other protective groups to be removed, an additional treatment is necessary. After the reduction, the catalyst is separated from the reaction mixture, for example by filtration.

The isoflavane may be purified after step (d), for example by a solvent evaporation, recrystallization, washing and/or drying. The purification step could be a final step of the overall process. The purification may use other known methods, such as chromatography or filtration. Purification steps may also be carried out at any stage of the inventive process for isolating or enriching intermediates, for example after reaction steps (a), (b) or (c).

Preferably, the isoflavone used as the starting compound of the inventive process in step (a) does not have free hydroxy groups, or other reactive groups except for the 4-keto group. Such free hydroxy groups could react in the inventive process. It is preferred that protective groups are covalently attached to the hydroxy groups, or any other reactive groups. In a preferred embodiment, the protective groups are attached to the hydroxy groups of the isoflavone in a preceding step (a0). Protective groups for covalent attachment to hydroxy groups are known in the art. For example, they may be selected, attached and removed as described in "Greene's Protective Groups in Organic Synthesis"; Peter G. M. Wuts, Theodora Greene, publisher: Wiley, 2006.

Preferably, the protective group is selected from acyl having 1 to 10 carbon atoms, preferably acetyl; alkoxycarbonyl wherein the alkoxy group has 1 to 10 carbon atoms, preferably 1 to 5 carbon atoms, more preferably 1 or 2 carbon atoms; alkyl having 1 to 10 carbon atoms, preferably methyl, ethyl, propyl or tert-butyl; a cyclic group comprising 1 to 20 carbon atoms, such as tetrahydrofuran, cyclic alkyl having 5 to 10 carbon atoms, benzyl or benzoyl; an ether group having 1 to 10 carbon atoms, such as methoxymethyl (MOM) or 2-methoxy-ethoxymethyl (MEM); a diol, such as an 1,2- or 1,3-diol, having 2 to 10 carbon atoms, toluenesulfonyl (tosyl); or silyl, such as trimethylsilyl.

In the inventive process, an isoflavane can be obtained from a corresponding isoflavone at high enantiomeric purity and total yield. Preferably, the enantiomeric purity of the isoflavane in the inventive process is at least 5% (ee), at least 10% (ee), at least 20% (ee), at least 40% (ee), at least 60% (ee), at least 75% (ee), at least 90% (ee) or at least 95% (ee), more preferably at least 98% (ee) or at least 99% (ee). Of course, a higher enantiomeric yield is preferred. Nonetheless, even a low enantiomeric excess can be advantageous as a starting point for further separation by recrystallization. Preferably, the total yield of the chiral isoflavane is at least 5%, at least 10% or at least 15%, based on the corresponding amount of isoflavone provided in step (a).

In a preferred embodiment, the inventive method comprises additional production of another isoflavane fraction, such as an isoflavane racemate, or a mixture of the R- and S-form of an isoflavane, in which one component is enriched. Such an additional isoflavane fraction can be obtained from residual chiral intermediate dissolved in the mother liquor of the crystallization in step (b1), which has been depleted from a desired precipitated isoflavane. Thereby, this chiral intermediate dissolved in the mother liquor, optionally after precipitation and further purification, is also converted into corresponding isoflavane in subsequent steps (c) and (d). When proceeding accordingly, the overall process is more economical.

In a preferred embodiment of the invention, reagents or catalysts are recycled. Preferably, the palladium/carbon catalyst is recycled and reused in the process. Further, it is preferred to recycle the chiral agent, especially after detachment from the chiral intermediate, and reuse it in the overall process. When proceeding accordingly, the overall process costs can be lowered.

In another preferred embodiment, chiral and/or amine intermediates, which are not the desired stereoisomers, are returned into the process. This can be done by cleaving off all chiral, amine and protective groups to obtain the unprotected 4-hydroxy intermediate. The 4-hydroxy intermediate comprising 3 free hydroxy groups can then be selectively modified with protective groups. This procedure renders the overall process more efficient.

It is preferred to use daidzein as the isoflavone. From daidzein, a reaction product is obtained which is enriched in S-equol or R-equol. As a natural product, daidzein is available in large amounts, for example from soy extracts. Therefore, an inventive method for producing R-equol or S-equol has the advantages that the starting compound is inexpensive and easily available.

It is possible to use any isoflavone as starting compound. Isoflavones and isoflavanes applicable in the inventive process are for example those, in which the basic structure (as shown in formula (I), (II) or (III) above) has further substituents attached to one or both phenyl rings, especially hydroxy, alkyl or alkoxy, or aryl, araryl, halogen, nitro, sulfate, sulfonate, hydroxamate or amine groups. The alkyl or alkoxy substituents may comprise 1 to 10 carbon atoms and are branched or linear, preferably methyl, ethyl, propyl, isopropyl or butyl, or methoxy, ethoxy, propoxy or butoxy. Further applicable isoflavones are those, in which the hydroxy groups are esterified or etherified. Suitable isoflavones are, for instance, daidzein, 3'-hydroxydaidzein for the synthesis of 3'-hydroxyequol, 2',3'-hydroxydaidzein for the synthesis of 2',3'-hydroxyequol and 4'-methoxy-2'-hydroxydaidzein for the synthesis of vestitol (4'-methoxy-2'-hydroxyequol). Preferred derivatives, isoflavones and isoflavanes for use in the inventive process are those, which have a specific physiological activity. Any substituent should not interfere with or impair the inventive process.

For example, derivatives of daidzein can be used as starting compounds. As the reaction product, the corresponding derivative of equol will be obtained. The term "derivative" as used herein especially relates to substances which have the same basic structure as daidzein or equol and comprise at least one additional substituent, or lack a substituent. Derivatives can be compounds, in which the hydroxy groups are not, or not exclusively, at the 4'- and 7-position, but at different or additional positions, for instance at the 5'- and 6'-position. Derivatives can have additional hydroxy groups, or alkoxy- or alkyl groups having 1 to 10 carbon atoms.

Subject of the invention is also a method for producing an isoflavane, comprising the steps:
(c0) providing a chiral intermediate as defined above,
(c) reacting the chiral intermediate with an amine reagent, such that an amine group is covalently attached to the C4-position, whereas the chiral group is removed from the C4-position, thereby obtaining an amine intermediate,
(d) reducing the amine intermediate at the C4-position to obtain a —CH$_2$— group at the C4-position,
wherein during or after step (c) or (d), the protective groups are removed from the hydroxy groups.

Steps (c0), (c) and (d) are carried out in consecutive order. The chiral intermediate is preferably produced according to steps (a) and (b) as outlined above. However, the chiral intermediate may also be produced by another method, if applicable. The reagents, such as protective group, chiral group, isoflavone, amine reagent and reducing agent, are characterized as outlined further above for the inventive process.

As outlined above, the chiral intermediate has a chiral group covalently attached to the C4-position. It is assumed that the chiral C4 carbon has four substituents, which are a H, the chiral group and two ring carbon atoms of the basic structure. Preferably, the chiral intermediate provided in step (c0) has the formula (IV) or (V):

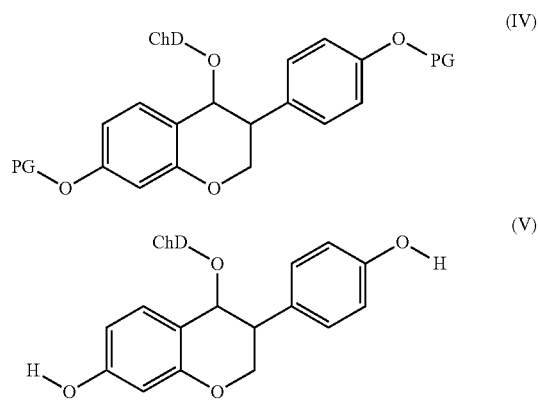

wherein

PG is a protective group, which is selected as outlined above, preferably alkyl or acyl having 1 to 10 carbon atoms, ChD is a chiral group comprising 8 to 30 carbon atoms, which preferably comprises at least one organic ring, and wherein the basic structure corresponding to the isoflavone can be substituted, preferably at the C5-, C7-, C3'- and/or C4'-position with —OH or —O-PG, wherein PG is a protective group as above.

Subject of the invention are also chiral intermediates and amine intermediates as defined above. Preferably, the chiral intermediate is one of formula (Ib) above. Preferably, the chiral intermediate is a compound of any of formulas (IV) to (V) and the amine intermediate is a compound of any of formulas (VI) to (VII):

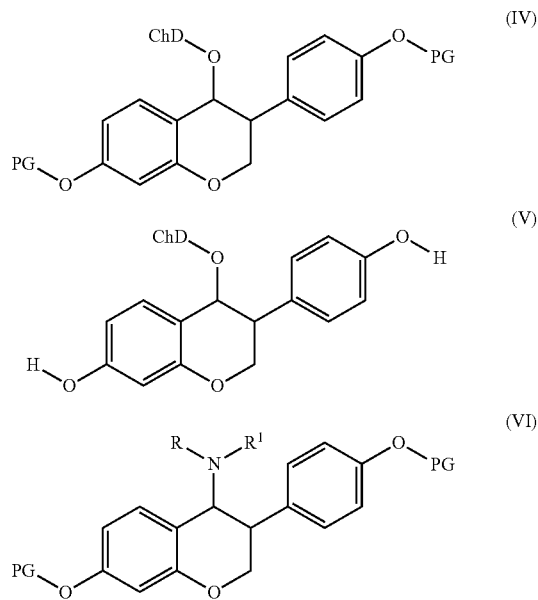

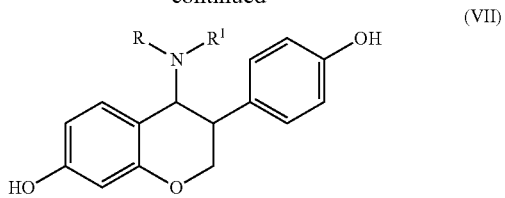

(VII)

wherein PG is a protective group as outlined above, preferably alkyl or acyl having 1 to 10 carbon atoms, ChD is a chiral group comprising 8 to 30 carbon atoms, which preferably comprises at least one organic ring. The chiral group may comprise 1 to 8 heteroatoms, such as O, N, or S. Preferably, the chiral group is linked to the C4-carbon atom by a C—C single bond. Preferably, the linkage between the C4-carbon and the chiral group is an ester bond.

RR$^1$N— is a secondary amine, preferably a cyclic amine having 5 to 20 carbon atoms or a non-cyclic amine, preferably a dialkylamine, wherein each alkyl group has 1 to 20 carbon atoms, wherein the cyclic amine may comprise one or more heteroatoms, especially O or S, and wherein the basic structure corresponding to the isoflavone can be substituted, preferably at the C5-, C7-, C3'- and/or C4'-position with —OH or —O-PG, wherein PG is a protective group as above. The substituents, such as protective group, chiral group, and amine group are characterized as outlined further above for the inventive process.

Specific embodiments of the inventive compounds are chiral intermediates and amine intermediates as disclosed further above with respect to the inventive process. These chiral and amine intermediates are important intermediates for carrying out the inventive process. They are relatively stable and can be isolated, purified, dried and stored for further use. With such stable intermediates, the process steps can be carried out at different time points, if desired. Such stable intermediates could also be modified in intermediate steps. The intermediates may or may not comprise protective groups.

Specific preferred intermediates of the invention are those of formula (IV) and (V) in which the chiral group ChD is the reaction product with (acetyloxy)(phenyl)acetic acid, N-p-tosyl-L-proline or N-(4-fluorophenyl)sulfonyl-L-proline, and of formula (VI) and (VII) in which the residue RNR$^1$ is morpholine. In these embodiments, PG is preferably acetyl.

In a highly preferred embodiment, the chiral reagent is selected from or naproxen or a corresponding activated compound.

The invention solves the problems underlying the invention. A new, simple and effective method for enantioselective production of R- and S-isoflavanes, such as R- and S-equol, is provided. S- or R-equol can be obtained at high enantiomeric purity. The total yield for five steps was about 11%. Such a yield is typical for such processes with multiple reaction steps and separation of stereoisomers. The reaction steps are simple. Most reagents are cheap and easily available. The more expensive reagents, for example Pd catalyst and the chiral reagent, such as naproxen, can be recycled. Toxic or harmful reagents, which are difficult to remove from the product, are not required. Parallel production of racemic (or low enantiomeric excess) equol is also possible, which can decrease expenses.

EXAMPLES

Examples 1 to 5: Synthesis of Equol from Daidzein by a Process According to the Invention The compounds and intermediates are shown in scheme 1 above.

Example 1: Synthesis of Diacetyl Daidzein (2)

A mixture of daidzein (2.54 g, 10 mmol) and acetic anhydride (5 ml) was stirred at reflux for 3 hours until a clear solution formed. After cooling isopropanol (20 ml was added and the suspension was stirred for 1 hour at r.t. The precipitate of 2 was filtered off, washed with isopropanol and dried on air. The yield of compound 2 was 3.26 g (9.65 mmol, 96.5%).

Example 2: Synthesis of Diacetyl Tetrahydrodaidzein (3)

A mixture of diacetyl daidzein (2) (3.26 g, 9.65 mmol), dioxane (50 ml) and 10% Pd/C catalyst (0.32 g) was stirred in steel autoclave with Teflon beaker in hydrogen atmosphere (pressure—3 kg/cm$^2$) at r.t. for 24 hours. After releasing from hydrogen the reaction mixture was checked by TLC (no starting material, main product—diacetyl tetrahydrodaidzein (3), traces of diacetyl dihydrodaidzein and diacetyl equol are possible).

The catalyst was filtered off, washed with dioxane, and the filtrate was evaporated to dryness in vacuum. Isopropanol (15 ml) was added to the residue and the mixture was stirred for 1 hour. The precipitate of 2 was filtered off, washed with isopropanol and dried on air. The yield of 3 was 2.68 g (7.82 mmol, 81%). The reaction time and temperature have to be defined by preliminary experiments for each batch of the catalyst.

Example 3: Synthesis of Naproxene Derivative 4SSR

Naproxene chloride (1.95 g, 7.82 mmol) was dissolved in dry pyridine (10 ml) and diacetyl tetrahydrodaidzein (3) (2.68 g, 7.82 mmol) was added. After stirring for 1 day at r.t. pyridine was evaporated in vacuum and the residue was crystallized from 2-propanol (25 ml). After cooling and staying for 1 hour at r.t. the precipitate was filtered off and washed with 2-propanol (3 ml). The precipitate was suspended in boiling 2-propanol (15 ml), the insoluble part was filtered off while hot, washed with hot 2-propanol (3 ml) and dried on air. The yield of naproxene derivative 4SRR was 0.80 g (1.44 mmol, 18.4%). M.p.—168-70° C.

Example 4: Synthesis of 3-(4-hydroxyphenyl)-4-(morpholin-4-yl)-3,4-dihydro-2H-chromen-7-ol (11)

The solution of compound 4SRR (0.80 g, 1.44 mmol) and morpholine (0.8 ml) in dioxane (4 ml) was stirred for 1 day at r.t. The reaction mixture was diluted with water (30 ml), stirred for 20 min, the precipitate was filtered off, washed with water and dried on air. Yield of compound 11 was 0.43 g (1.31 mmol, 91%). Acetic acid (3 ml) was added to the filtrate. The precipitate of naproxene was filtered off, washed with water and dried on air. The yield of naproxene was 0.32 g (1.37 mmol, 95%).

Example 5: Synthesis of R-equol (7R)

A mixture of 3-(4-hydroxyphenyl)-4-(morpholin-4-yl)-3,4-dihydro-2H-chromen-7-ol (11) (0.43 g, 1.31 mmol), ethanol (15 ml) and 10% Pd/C catalyst (50 mg) was treated at stirring by hydrogen (pressure—3 kg/cm$^2$) for 1 day in steel autoclave with Teflon beaker. The catalyst was filtered off, washed with ethanol (3 ml) and the filtrate (together with the rinse) was evaporated to dryness. The residue was dissolved in acetic acid (2 ml) and water (20 ml) was added to the solution. After 1 hour of stirring at r.t. the residue of R-equol was filtered off, washed with water (10 ml) and dried on air. The yield of R-equol (7R) was 0.30 g (1.22 mmol, 93%). Purity was found to be >=98% and enantiomeric purity 99.7%.

Examples 6 to 9: Reaction Mechanism and Optimization of the Inventive Process

The following examples 6 to 9 supplement the specific synthesis described above in examples 1 to 5. They were carried out for optimizing and understanding the reaction process. In examples 6 to 9, a preliminary reaction pathway and mechanism is proposed, which may explain the result, and could be used for optimizing the inventive process. The experiments provide an explanation why the overall process yields isoflavanes at high enantiomeric and total yield. However, the proposed pathway is preliminary and shall not limit the scope of the inventive process.

Example 6: Reduction of Diacetyl Daidzein

Scheme 2 below shows a possible reaction pathway for reducing diacetyl daidzein 2.

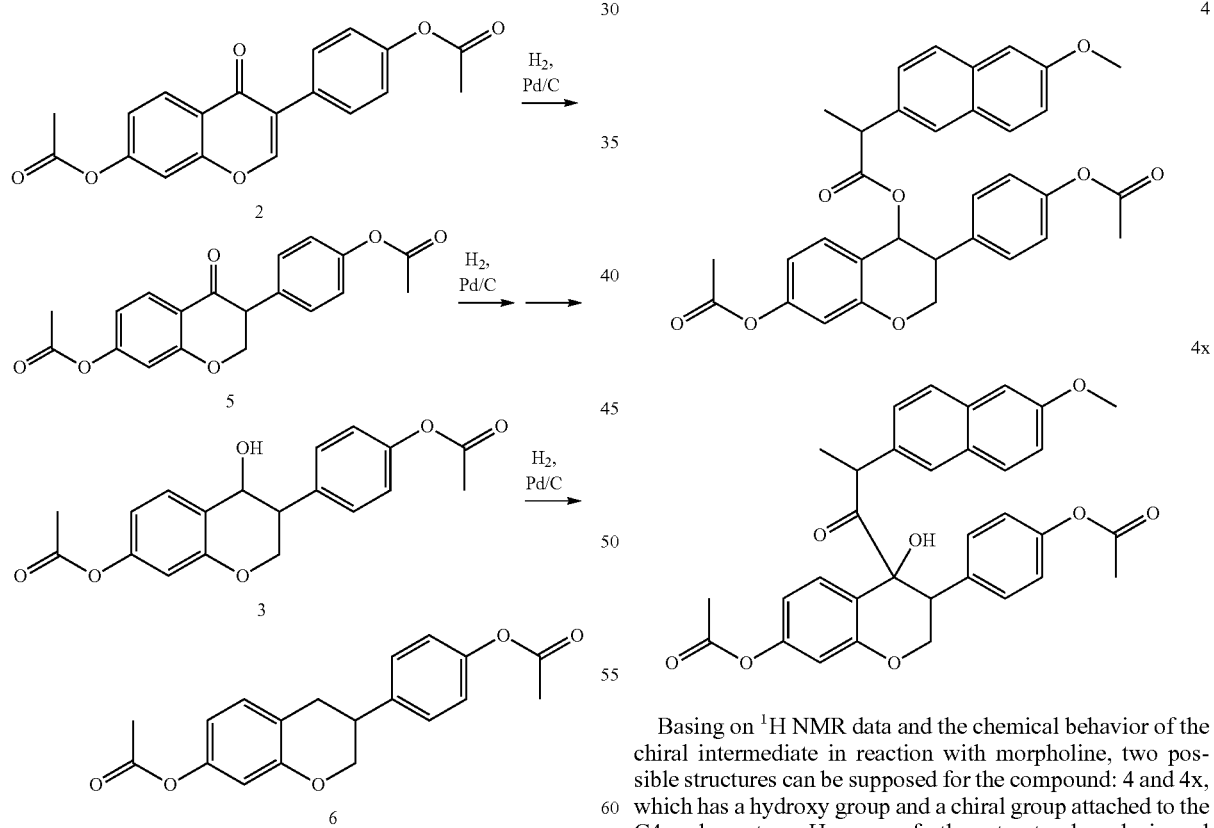

The catalyst has to be optimized for a high yield of desired intermediate 3, whilst further reaction to isoflavane 6 is to be avoided in this step. A high yield of compound 3 is achievable when optimizing the conditions, especially amount of palladium catalyst, reaction time and temperature. Reduction of diacetyl daidzein 2 at 25° C. for 5 hours by $H_2$ (pressure—5 kg/cm$^2$) with Pd/C catalyst gave a mixture of compounds 5 (~80%), 3 (~20%) and traces of the starting material. Increasing the reaction time to 20 hours gave practically no changes. Raising the temperature to 75-80° C. lead to formation of enough pure (>90% by TLC and $^1$H NMR) intermediate 3, which was successfully used in the following steps. It was noted that raising the temperature in process of hydrogenation of intermediate 2 did not lead to 'overhydrogenation' with formation of substantial amounts of diacetyl equol 6, as one may have expected. The results show that it is possible to adjust optimal conditions for hydrogenation of diacetyl daidzein 2 with catalysts different in activity by varying the temperature and reaction time and pressure of hydrogen. Pearlman catalyst (20% Pd(OH)$_2$ on charcoal) was also tested. Even at 25° C., hydrogenation of diacetyl daidzein 2 gave diacetyl equol 6. So the Pearlman catalyst seems to be too active to be applied in this reaction step.

Example 7: Synthesis of Naproxene Derivative

S-Naproxene was used for producing R-equol. It is known unambiguously that usage of R-naproxene would lead to S-equol in the same conditions with the same yield. Synthesis of a chiral intermediate was carried out according to example 2 above. The chiral intermediate has structure 4:

Basing on $^1$H NMR data and the chemical behavior of the chiral intermediate in reaction with morpholine, two possible structures can be supposed for the compound: 4 and 4x, which has a hydroxy group and a chiral group attached to the C4-carbon atom. However, further structural analysis and experiments on the reaction pathway confirmed that the chiral intermediate has structure 4. The chiral intermediate was prepared again and purified by crystallization from dioxane. The purity was confirmed by $^1$H NMR. A crystal of the compound was grown. X-ray analysis provided evidence that the structure corresponds to formula 4SRR:

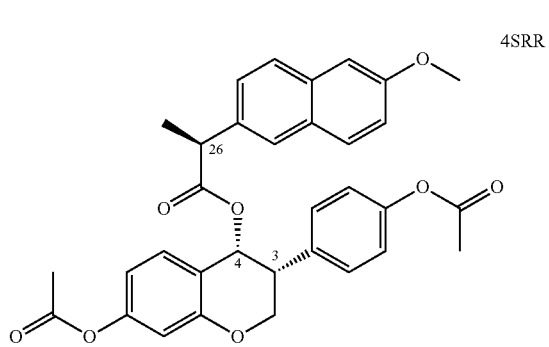 [SMILES: COc1ccc2cc([C@H](C)C(=O)O[C@H]3c4ccc(OC(C)=O)cc4OC[C@H]3c3ccc(OC(C)=O)cc3)ccc2c1]

4SRR

The result was confirmed by further experimental studies, in which chiral intermediates were prepared from batches of 4-hydroxyl intermediates with different ratios of stereoisomers. Overall, it was confirmed that the structure of the chiral intermediate corresponded to formula 4 above. However, it cannot be finally excluded that the reaction could also follow a different reaction pathway, at least under certain conditions or with certain reagents. The intermediate structure is practically not relevant, because both intermediates 4 and 4x would be applicable for producing chiral isoflavanes from isoflavones.

Example 8: Synthesis of Amine Intermediate 11

Intermediate 4SRR was converted into the amine intermediate 11 with morpholine according to example 4 above. Purity of the resulting amine derivative 11 was checked by $^1$H NMR and TLC. A crystal was grown and X-ray analysis was made. It was found that the amine intermediate is compound 11, wherein substituents at C3 and C4 are in the trans configuration.

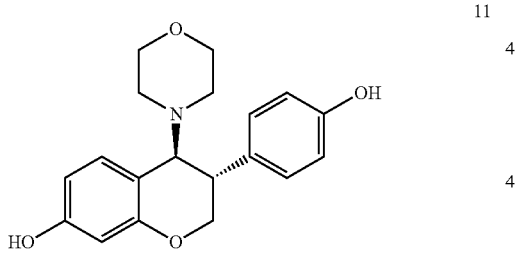

11

In further experiments, it was found that the trans configuration of the amine intermediate was obtained even when starting from chiral intermediate comprising stereoisomers in the trans and cis form. Probably, bulky substituents at C7 and C8 atoms stabilize trans-configuration of resulting product 11. But in any case, the chiral configuration at the C3 atom remains unchanged, because in the following step pure R-equol was obtained. So for practical means, the behavior of the C4 center in this reaction is not important.

Example 9: Reduction to R-Equol 7R

Hydrogenation of compound 11 required a sufficient amount of active catalyst in the final reduction step (scheme 3). When the a catalyst with low activity was used, after 2 days of reduction by hydrogen (pressure—3 kg/cm$^2$) in ethanol at 25° C. approximately 50% of the starting material remained unreacted. Highly active Pd/C or Pearlman catalyst Pd(OH)$_2$/C was found to be suitable. With Pearlman catalyst, all starting material was reduced at 25° C. in 6 hours (H$_2$ pressure—3 kg/cm$^2$). The purity of resulting R-equol was determined by $^1$H NMR spectrum to be >98%, and chiral analysis gave 99.7% of R-enantiomer. Such high enantiomeric purity is an evidence for that no racemization occurs during the last two reaction steps.

Scheme 3: Reduction to R-equol

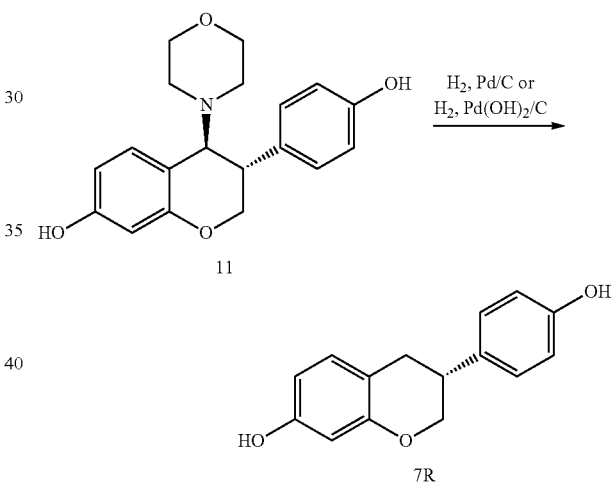

Example 10: Alternative Pathways for Producing 4-Hydoxy Intermediate

At least three different pathways shown in scheme 4 below lead to 4-hydroxyl intermediate 3G:

Scheme 4: Pathways for preparing 4-hydroxy intermediate

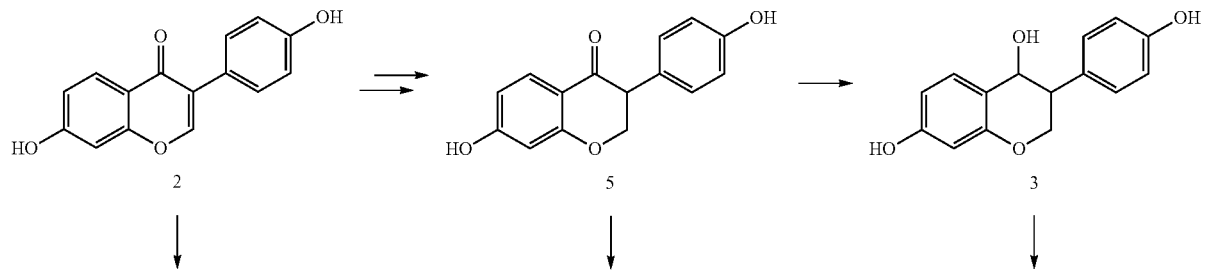

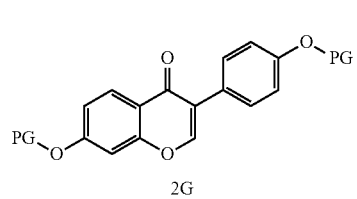 2G

-continued

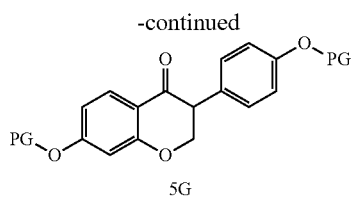 5G

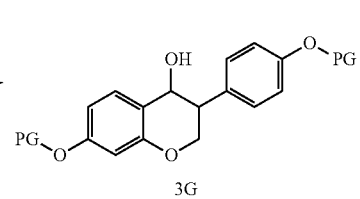 3G

In the working examples above, a first pathway (2→2G→5G→3G) was used. A second pathway (2→5→5G→3G) is also possible. Reaction step (2→5) is described in Waehaelae et al., Journal of Organic Chemistry, 1997, vol 62, p 7690-7693. Reaction step (5→5G) is described in Amari et al., Bioorganic and Medicinal Chemistry, 2004, vol 12, #14, p 3763-3782. The reaction step (5G→3G) corresponds to the first pathway and is described above. A third pathway (2→5→3→3G) is also possible. Synthesis of tetrahydrodaidzein 3 is widely described in the literature, for example in Pihlaja et al., Journal of Organic Chemistry, 2003, vol 68, #18 p 6864-6869. This compound has 3 hydroxy groups and only 2 protecting groups are to be selectively attached. Tetrahydrodaidzein 3 was treated with a controlled amount of acetylating reagent in a hope that phenolic hydroxyls will be acetylated selectively. As one could expect, using of a great excess of acetylation reagent lead to the formation of triacetyl derivative as the sole product. The structure was confirmed by $^1$H NMR data. With 2.2 moles of acetyl chloride, a mixture containing 69-70% of the desired O,O'-diacetyltetrahydrodaidzein (corresponding to 3G) and 30-31% of the side product O,O',O'-triacetyltetrahydrodaidzein was obtained. The desired product can be separated and used for further production of equol. The results demonstrate that acyl protective groups can be selectively introduced onto phenolic hydroxyls of tetrahydrodaidzein 3 with formation of a product which can be used in the further reaction with chiralizing reagent. This result is also important, because it opens up the possibility to return racemic chiral or amine intermediates, which are not the desired stereoisomers, back into the process. This can be done by cleaving off all chiral, amine and protective groups to obtain the unprotected 4-hydroxyl intermediate. The 4-hydroxyl intermediate comprising 3 free hydroxy groups can then be selectively modified with protective groups. This procedure renders the overall process more efficient.

Example 11 and 12: Attachment of Alternative Protective Groups to Daidzein

Compounds 2b and 2f were prepared comprising alternative protective groups. The formulae of both products are shown in scheme 5 below.

Example 11: O,O'-bis(ethoxycarbonyl)daidzein (2b)

A mixture of daidzein (5.08 g, 20 mmol), dry dioxane (70 ml), ethyl chloroformate (10 ml, 105 mmol) and triethylamine (15 ml, 108 mmol) was stirred at r.t. for 1 day. Water (800 ml) was added and the resulting suspension was stirred for 30 min. The precipitate was filtered off, washed with water and dried on air. The yield of O,O'-bis(ethoxycarbonyl)daidzein (2b)—7.66 g (19.2 mmol, 96%).

Example 12: O,O'-bis(methoxycarbonyl)daidzein (2f)

To a stirred suspension of daidzein (5.28 g, 20.78 mmol) in dry dioxane (120 ml), methyl chloroformate (10 ml, 129 mmol) was added. To the stirred mixture Et$_3$N (18 ml, 129 mmol) was added dropwise with cooling on the water bath at 50-60° C. After Et$_3$N is added, the bath is removed and reaction mixture is stirred for additional 3 hr at room temperature. The precipitate is filtered off, washed with some dioxane, crystallized from AcOH, washed with plenty of water and dried to give 6.14 g (16.6 mmol, 80%) of desired product.

In further experiments, protective groups —CO—O-ethyl, —CO-butyl or —CO-phenyl were also attached selectively to the 4' and 7'hydroxy groups of daidzein.

Example 13: O,O'-diacetyltetrahydrodaidzein (3a)—Variant with Additional Reduction with NaBH$_4$ A mixture of diacetyl daidzein (2a) (32 g, 94.6 mmol), dioxane (600 ml) and 10% Pd/C catalyst (3.2 g) was stirred in stainless steel autoclave in hydrogen atmosphere (pressure—3 kg/cm$^2$) at 50-60° C. for 4-8 hours until no starting material 2a was detected by TLC. After the autoclave was depressurized, the catalyst was filtered off, washed with dioxane, and sodium borohydride (11.3 g, 0.3 mol) was added to the filtrate. The mixture was stirred for 3-6 hours, the solids were filtered off, washed with dioxane (the rinse was added to the filtrate) and acetic acid (3 ml) was added to the solution. The solvent was evaporated to dryness in vacuum. Ethanol (250 ml) was added to the residue and the mixture was kept overnight in refrigerator. The precipitate of 3a was filtered off, washed with ethanol and dried on air. The yield of 3a—22.5 g (65.7 mmol, 69.5%). By TLC and $^1$H NMR data the product 3a was identified.

Examples 14 and 15: Preparation of Alternative 4-Hydoxy Intermediates

Daidzein derivatives 2b and 2f with alternative protective groups at the 4' and 7' position prepared according to examples 11 and 12 were reacted to 4-hydroxyl intermediates as shown in scheme 5 below.

Scheme 5: Preparation of 4-hydroxy intermediates

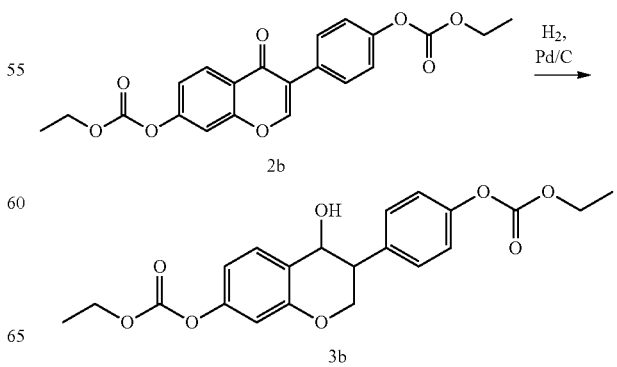

2b

3b

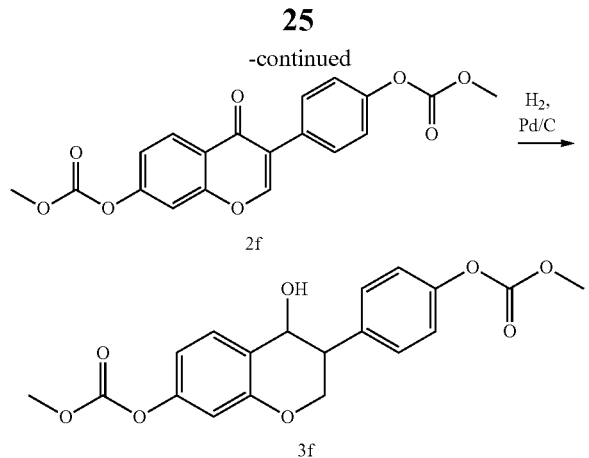

Example 14: O,O'-bis(ethoxycarbonyl)tetrahydrodaidzein (3b)

The reaction time and temperature were defined by preliminary experiments for each batch of the catalyst. A mixture of O,O'-bis(ethoxycarbonyl)daidzein (2b) (2.1 g, 5.27 mmol), dioxane (40 ml) and 10% Pd/C catalyst (0.22 g) was stirred in steel autoclave with Teflon beaker in hydrogen atmosphere (pressure was 5 kg/cm$^2$) at r.t. for 2 days. After depressurizing the reaction mixture was checked by TLC (no starting material, main product, O,O'-bis(ethoxycarbonyl)tetrahydrodaidzein (3b) was detected; traces of O,O'-bis(ethoxycarbonyl)dihydrodaidzein and O,O'-bis(ethoxycarbonyl)equol were possible). The catalyst was filtered off, washed with dioxane, and the filtrate was evaporated to dryness in vacuum. Ethanol (20 ml) was added to the residue and the mixture was allowed to stay overnight at r.t. The precipitate of 3b was filtered off, washed with ethanol and dried on air. The yield of 3b was 1.68 g (4.17 mmol, 79%). See $^1$H NMR in picture 1.

In a further experiment, the reaction was carried out with daidzein having —O—CO—O—CH$_2$CH$_3$ protective groups attached to the C4' and C7' of daidzein.

Example 15: O,O'-Bis(methoxycarbonyl)tetrahydrodaidzein (3f)

The reaction time and temperature were defined by preliminary experiments for each batch of the catalyst. A mixture of O,O'-bis(methoxycarbonyl)daidzein (2f) (1.85 g, 5 mmol), dioxane (40 ml) and 10% Pd/C catalyst (0.20 g) was stirred in steel autoclave with Teflon beaker in hydrogen atmosphere (pressure was 5 kg/cm$^2$) at 60-70° C. for 6 hours. After cooling and depressurizing the reaction mixture was checked by TLC (no starting material, main product, O,O'-bis(methoxycarbonyl)tetrahydrodaidzein (3b) was detected; traces of O,O'-bis(methoxycarbonyl)dihydrodaidzein and O,O'-bis(methoxycarbonyl)equol were possible). The catalyst was filtered off, washed with dioxane, and the filtrate was evaporated to dryness in vacuum. Ethanol (20 ml) was added to the residue and the mixture was allowed to stay overnight in refrigerator. The precipitate of 3f was filtered off, washed with ethanol and dried on air. The yield of 3f was 1.39 g (3.71 mmol, 74%).

Examples 16 to 22: Synthesis of Equol with Various Chiral Reagents

Equol was prepared with different chiral reagents according to the reaction pathway in scheme 6 below. The standard protocol used in all cases was the following: the chiral reagent was converted into a carbonyl chloride (synthesized from an acid) or sulfonyl chloride, which interacted with O,O'-diprotected tetrahydrodaidzein 3G in pyridine at r.t. After evaporation of the excess of pyridine (or without it), the product 4G was separated by treatment of the residue with solvents and analyzed by $^1$H NMR method. The chiral intermediates 4G reacted with morpholine in dioxane at r.t. to form intermediates 11G. Reduction of derivatives 11G into equol 6 was done by hydrogen (P=5 kg/cm$^2$) at r.t. with 20% Pd(OH)$_2$/C as a catalyst.

Scheme 6: Reaction pathway examples 16 to 22

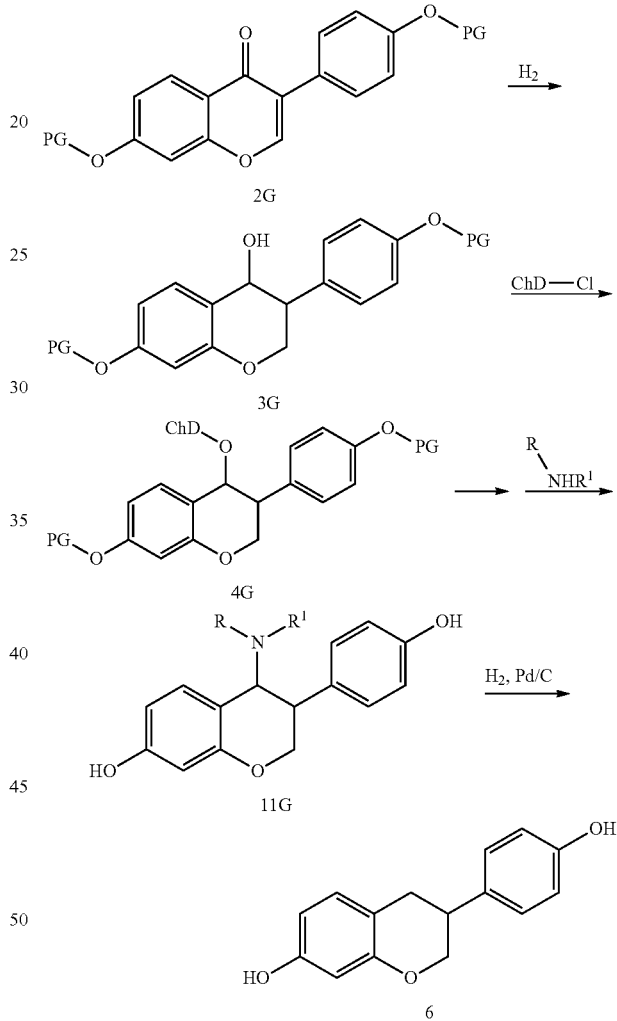

Chiral reagents, chiral intermediates 4G and yields of equol (values of enantiomeric excess ee, measured by angle of rotation of polarization plane method or content of S- or R-enantiomer measured by chiral HPLC) are summarized in table 1 below.

Example 16: 7-acetoxy-3-(4-acetoxyphenyl)chroman-4-yl (2R)-2-methoxy-2-phenyl-acetate (20)

A mixture of (R)-(−)-α-methoxyphenylacetic acid (13) (0.83 g, 5 mmol), dry benzene (10 ml), oxalyl chloride (1.56 g, 12.3 mmol) and 3 drops of DMF was stirred at r.t. for 1 day. Volatiles were evaporated to dryness in vacuum, and to the residue were added: at first pyridine (5 ml) and then O,O'-diacetyltetrahydrodaidzein (3a) (1.37 g, 4 mmol). After stirring for 1 day at r.t. the mixture was dissolved in hot 2-propanol (30 ml), cooled down and allowed to stay for 1 day in refrigerator. The precipitate of product 20 was filtered off (weight 1.52 g, 3.1 mmol, 77.5%) and dissolved in DCM (3 ml). 2-Propanol (5 ml) was added to the solution and the mixture was kept in refrigerator overnight. The precipitate was filtered off and the filtrate was evaporated to dryness to give derivative 20 as white solid. The yield of derivative 20 was 0.45 g (0.92 mmol, 23%).

Example 17: 7-acetoxy-3-(4-acetoxyphenyl)chroman-4-yl 2-acetoxy-2-phenylacetate (22)

A mixture of (2S)-(acetyloxy)(phenyl)acetic acid (17) (0.97 g, 5 mmol), dry benzene (10 ml), oxalyl chloride (1.25 ml, 14.6 mmol) and DMF (0.05 ml) was stirred at r.t. for 1 day.
Volatiles were evaporated to dryness in vacuum, and to the residue were added (with cooling on ice-water bath): at first pyridine (5 ml) and then O,O'-diacetyltetrahydrodaidzein (3a) (1.37 g, 4 mmol). After stirring for 1 day at r.t. the mixture was dissolved in hot 2-propanol (30 ml). The solution was cooled and kept in refrigerator for 3 hours. The precipitate was filtered off, washed with 2-propanol (3 ml) and dried on air. The yield of derivative 22 was 0.76 g (1.47 mmol, 37%).

Example 18: 7-acetoxy-3-(4-acetoxyphenyl)chroman-4-yl tosyl-L-prolinate (24)

A mixture of N-tosyl-L-proline (19) (1.35 g, 5 mmol), dry benzene (10 ml), oxalyl chloride (1.9 g, 14.8 mmol) and DMF (0.05 ml) was stirred at r.t. for 1 day. Volatiles were evaporated to dryness in vacuum, and to the residue were added: at first pyridine (5 ml) and then O,O'-diacetyltetrahydrodaidzein (3a) (1.37 g, 4 mmol). The mixture was stirred for 1 day at r.t. and dissolved in hot 2-propanol (50 ml). After cooling and staying for 1 day at r.t. the resin formed. The supernatant was poured off and the resin was crystallized from 2-propanol (30 ml). The resin formed again, the supernatant was poured off and the residue was refluxed for 15 min in hexane (20 ml). After cooling the precipitate was filtered off, washed with hexane and dried on air. The yield of crude derivative 24 was 0.93 g (1.51 mmol, 58%). This was crystallized from trichloroethylene (2 ml). The yield was 0.29 g (0.49 mmol, 12.2%).

Example 19: 7-((ethoxycarbonyl)oxy)-3-(4-((ethoxycarbonyl)oxy)phenyl)chroman-4-yl (2S)-2-(6-methoxynaphthalen-2-yl)propanoate (25)

A mixture of naproxene 16 (0.6 g, 2.61 mmol), dry benzene (5 ml) and oxalyl chloride (0.69 g, 5.43 mmol) was stirred at r.t. for 4 hours. Volatiles were evaporated to dryness in vacuum, and to the residue were added: at first pyridine (4 ml) and then O,O'-bis(ethoxycarbonyl)tetrahydrodaidzein (3b) (1.05 g, 2.61 mmol). The mixture was stirred for 1 day at r.t. and dissolved in hot 2-propanol (30 ml). After cooling and staying for 1 day at r.t. the resin formed. The supernatant was poured off and the resin was crystallized from 2-propanol (10 ml). The resin formed again, the supernatant was poured off and the residue was refluxed for 15 min in hexane (20 ml). After cooling the precipitate was filtered off, washed with hexane and dried on air. The yield of derivative 25 was 0.93 g (1.51 mmol, 58%).

Example 20: 7-acetoxy-3-(4-acetoxyphenyl)chroman-4-yl((4-fluorophenyl)sulfonyl)-L-prolinate (32)

A mixture of N-(4-fluorophenyl)sulfonyl-L-proline (31) (1.00 g, 3.66 mmol; prepared according to WO2010/141805 A1, page/page column 43-44), dry benzene (10 ml), oxalyl chloride (1.27 g, 10 mmol) and DMF (0.05 ml) was stirred at r.t. for 1 day. Volatiles were evaporated to dryness in vacuum, and to the residue were added (with cooling on ice-water bath): at first pyridine (3 ml) and then O,O'-diacetyltetrahydrodaidzein (3a) (1.0 g, 2.93 mmol). The mixture was stirred for 4 hours at r.t. and dissolved in hot 2-propanol (20 ml). After cooling and staying for 1 day at r.t. the resin formed. The supernatant was poured off and the resin was crystallized from 2-propanol (10 ml). The resin formed again, the supernatant was poured off, 2-propanol (10 ml) was added and the mixture was heated to boiling. Insoluble part was filtered off while hot, washed with 2-propanol and dried on air. The yield of derivative 32 was 0.68 g (1.14 mmol, 39%). This sample was additionally crystallized from dioxane (1.5 ml) to give 7-acetoxy-3-(4-acetoxyphenyl)chroman-4-yl ((4-fluorophenyl)sulfonyl)-L-prolinate (32) as very pure 32SSS enantiomer.

Example 21: 7-((Methoxycarbonyl)oxy)-3-(4-((methoxycarbonyl)oxy)phenyl)chroman-4-yl (2S)-2-(6-methoxynaphthalen-2-yl)propanoate (33)

A mixture of naproxene 16 (0.92 g, 4 mmol), dry benzene (5 ml) and oxalyl chloride (1.0 g, 7.9 mmol) was stirred at r.t. for 4 hours. Volatiles were evaporated to dryness in vacuum, and to the residue were added: at first pyridine (4 ml) and then O,O'-bis(methoxycarbonyl)tetrahydrodaidzein (3f) (1.39 g, 3.71 mmol). After stirring for 4 yours at r.t. the mixture was dissolved in hot 2-propanol (30 ml). After cooling and staying for 1 day at r.t. the resin formed. The supernatant was poured off and the resin was crystallized from 2-propanol (10 ml). The precipitate was filtered off, washed with 2-propanol (3 ml) and dried on air. The yield of derivative 33 was 1.0 g (1.7 mmol, 46%).

Example 22: 7-((Ethoxycarbonyl)oxy)-3-(4-((ethoxycarbonyl)oxy)phenyl)chroman-4-yl (2R)-2-methoxy-2-phenylacetate (35)

A mixture of (R)-(−)-α-methoxyphenylacetic acid (13) (0.42 g, 2.5 mmol), dry benzene (5 ml), oxalyl chloride (0.78 g, 6.14 mmol) and 2 drops of DMF was stirred at r.t. for 1 day. Volatiles were evaporated to dryness in vacuum, and to the residue were added: at first pyridine (2.5 ml) and then O,O'-bis(ethoxycarbonyl)tetrahydrodaidzein (3b) (0.8 g, 2 mmol). After stirring for 1 day at r.t. the mixture was dissolved in hot 2-propanol (15 ml), cooled down and allowed to stay for 1 day in refrigerator. The precipitate was filtered off and was crystallized once more from 2-propanol (5 ml). The yield of derivative 35 was 0.66 g (1.2 mmol, 60%). See $^1$H NMR spectrum in picture 8.
General Procedure for Synthesis of Amine Intermediate and Equol According to Examples 16 to 22:

3-(4-Hydroxyphenyl)-4-(morpholin-4-yl)-3,4-dihydro-2H-chromen-7-ol (11)

The solution of compound 4G (2 mmol) and morpholine (0.87 ml, 10 mmol) in dioxane (8 ml) was stirred for 1-2 days at r.t. After disappearance of the starting material (control by TLC), the reaction mixture was diluted with water (100 ml), stirred for 20 min, the precipitate was filtered off, washed with water and dried on air. Yield of compound 11 was 90-96%.

Equol (7)

A mixture of 3-(4-hydroxyphenyl)-4-(morpholin-4-yl)-3,4-dihydro-2H-chromen-7-ol (11) (0.65 g, 2 mmol), ethanol (30 ml) and 10% Pd/C catalyst (70 mg) was treated at stirring with hydrogen (at pressure 3-5 kg/cm$^2$) for 1 day in steel autoclave with Teflon beaker. The catalyst was filtered off, washed with ethanol (5 ml) and the filtrate (together with the rinse) was evaporated to dryness. Diluted acetic acid (0.5 ml in 20 ml of water) was added to the residue. After 1 hour of stirring at r.t. the precipitate was filtered off, washed with water and dried on air to give equol as white crystals. The yield was >90%.

TABLE 1

Chiral reagents and results

| Ex. | chiral reagent | chiral intermediate 4G | equol form | % ee |
|---|---|---|---|---|
| 9 | 16 | 4SRR | R | 99 |
| 16 | 13 | 20 | racemic | 0 |
| 17 | 17 | 22 | R | 6.1 |

TABLE 1-continued
Chiral reagents and results
| Ex. | chiral reagent | chiral intermediate 4G | equol form | % ee |
|---|---|---|---|---|
| 18 | 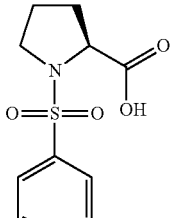 19 | 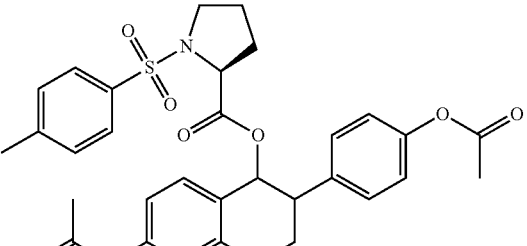 24 | S | 88 |
| 19 | 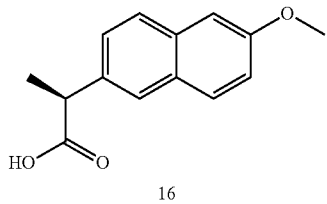 [SMILES: COc1ccc2cc([C@H](C)C(=O)O)ccc2c1] 16 | 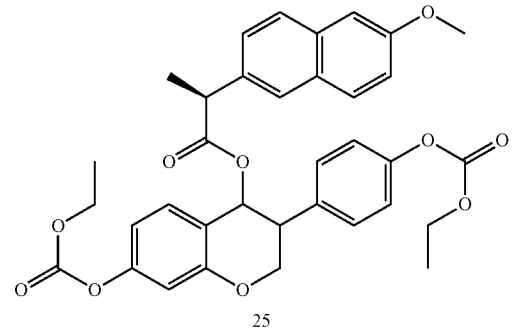 [SMILES: CCOC(=O)Oc1ccc(C2COc3cc(OC(=O)OCC)ccc3C2OC(=O)[C@@H](C)c2ccc3cc(OC)ccc3c2)cc1] 25 | R* | 8.5 |
| 20 | 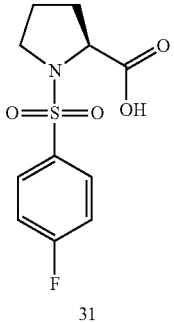 [SMILES: O=C(O)[C@@H]1CCCN1S(=O)(=O)c1ccc(F)cc1] 31 | 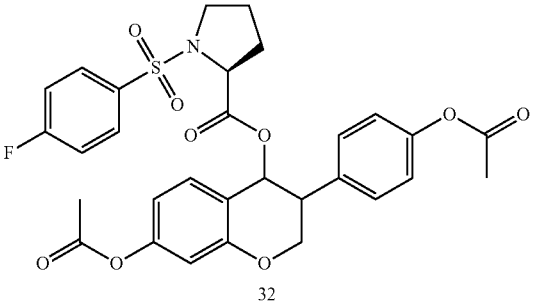 [SMILES: CC(=O)Oc1ccc(C2COc3cc(OC(C)=O)ccc3C2OC(=O)[C@@H]2CCCN2S(=O)(=O)c2ccc(F)cc2)cc1] 32 | S | 88 |
| 21 | 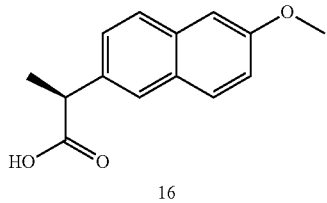 [SMILES: COc1ccc2cc([C@H](C)C(=O)O)ccc2c1] 16 | 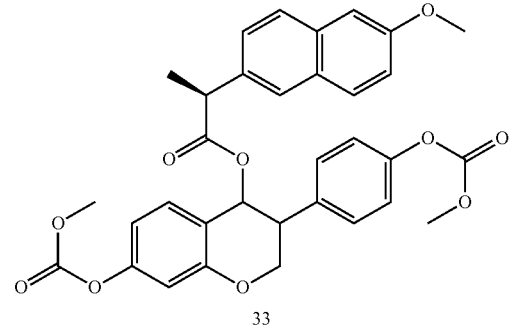 [SMILES: COC(=O)Oc1ccc(C2COc3cc(OC(=O)OC)ccc3C2OC(=O)[C@@H](C)c2ccc3cc(OC)ccc3c2)cc1] 33 | R* | 7.6 |

TABLE 1-continued

Chiral reagents and results

| Ex. | chiral reagent | chiral intermediate 4G | equol form | % ee |
|---|---|---|---|---|
| 22 | 13 | 35 | racemic | 0 |

The invention claimed is:

1. A method for enantioselective production of equol from daidzein, comprising the steps:
   (a) selectively reducing the daidzein, which may have protective groups covalently attached to the hydroxy groups, such that the 4-keto group of the daidzein is converted into a 4-hydroxy group, and the 2,3-double bond of the daidzein is converted to a 2,3-single bond, thereby obtaining a 4-hydroxy intermediate, and
   (b) reacting the 4-hydroxy intermediate with a chiral reagent, such that a chiral group is covalently attached to the C4-position of the 4-hydroxy intermediate, thereby obtaining a chiral intermediate, and
   (c) reacting the chiral intermediate with an amine reagent, such that an amine group is covalently attached to the C4-position, whereas the chiral group is removed from the C4-position, thereby obtaining an amine intermediate.

2. The method of claim 1, comprising a step (d) following step (c):
   (d) reducing the amine intermediate at the C4-position of to obtain a —CH$_2$— group at the C4-position.

3. The method of claim 1, comprising a step (a0) preceding step (a):
   (a0) covalently attaching protective groups to the hydroxy groups of the daidzein,
or a step (b0) or (b0a) preceding step (b):
   (b0) covalently attaching protective groups to the hydroxy groups of the 4-hydroxy intermediate or to the hydroxy groups of an intermediate isoflavanone,
   (b0a) covalently attaching protective groups to the hydroxy groups of a precursor of the 4-hydroxy intermediate, of which the 2,3-double bond was already selectively reduced to a 2,3-single bond.

4. The method of claim 3, wherein during or after step (c), the protective groups are removed from the hydroxy groups.

5. The method of claim 1, comprising a step (b1) following step (b):
   (b1) separating diastereomers of the chiral intermediate.

6. The method of claim 1, comprising the steps:
   (a0) covalently attaching protective groups to the hydroxy groups of the daidzein,
   (a) selectively reducing the daidzein, such that the 4-keto group of the daidzein is converted into a 4-hydroxy group, and the 2,3-double bond of the daidzein is converted to a 2,3-single bond, thereby obtaining a 4-hydroxy intermediate,
   (b) reacting the 4-hydroxy intermediate with a chiral reagent, such that a chiral group is covalently attached to the C4-position of the 4-hydroxy intermediate, thereby obtaining a chiral intermediate,
   (b1) separating diastereomers of the chiral intermediate by crystallization,
   (c) reacting the chiral intermediate with an amine reagent, such that an amine group is covalently attached to the C4-position, whereas the chiral group is removed from the C4-position, thereby obtaining an amine intermediate,
   (d) reducing the amine intermediate at the C4-position of to obtain a —CH$_2$— group at the C4-position, and
wherein during or after step (c) or (d), the protective groups are removed from the hydroxy groups.

7. The method of claim 1, wherein the reduction in step (a) is carried out in the presence of a metal catalyst selected from palladium/carbon, Raney nickel, platinum (IV) oxide and Pd(OH)$_2$, and/or a reducing reagent selected from hydrogen, ammonium formate, formic acid and cyclohexene.

8. The method of claim 1, wherein the chiral reagent in step (b) comprises an activated acid group and at least one ring.

9. The method of claim 8, wherein the chiral reagent has 8 to 30 carbon atoms, a chiral carbon atom, optionally 1 to 8 heteroatoms; and 1 to 5 rings, and comprises an activated acid group.

10. The method of claim 1, wherein the amine reagent in step (c) is a secondary amine.

11. The method of claim 1, wherein the amine reagent in step (c) is selected from morpholine, C-substituted morpholine, pyrrolidine, N-substituted piperazine, piperidine, dimethylamine and diethylamine.

12. The method of claim 2, wherein the reduction in step (d) is carried out in the presence of a metal catalyst selected from palladium/carbon, Raney nickel, platinum (IV) oxide and Pd(OH)$_2$, and/or a reducing reagent selected from hydrogen, ammonium formate, formic acid and cyclohexene.

13. The method of claim 1, wherein the protective group is selected from acyl having 1 to 10 carbon atoms; alkyl; a cyclic group; an ether group having 1 to 10 carbon atoms; a diol having 2 to 10 carbon atoms; toluylsulfonyl; or silyl.

14. A method for producing equol, comprising the steps:
- (c0) providing a chiral intermediate obtainable according to claim 1,
- (c) reacting the chiral intermediate with an amine reagent, such that an amine group is covalently attached to the C4-position, whereas the chiral group is removed from the C4-position, thereby obtaining an amine intermediate,
- (d) reducing the amine intermediate at the C4-position to obtain a —$CH_2$— group at the C4-position, wherein during or after step (c) or (d), the protective groups are removed from the hydroxy groups.

15. The method of claim 14, wherein the chiral intermediate has formula (IV) or (V):

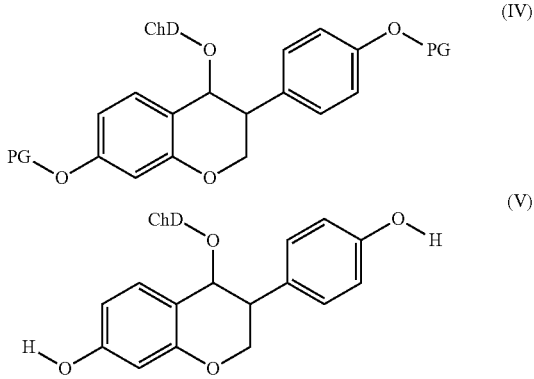

wherein
PG is a protective group, and
ChD is a chiral group having 8 to 30 carbon atoms.

16. The method of claim 1, wherein equol is obtained at an enantiomeric purity of at least 5% e.e.

17. The method of claim 10, wherein the secondary amine is a cyclic amine having 5 to 20 carbon atoms or a non-cyclic dialkylamine, wherein each alkyl group has 1 to 20 carbon atoms.

18. The method of claim 13, wherein the protective group is selected from acetyl; methyl, ethyl, propyl or tert-butyl; tetrahydrofuran, cyclic alkyl having 5 to 10 carbon atoms, benzyl or benzoyl; methoxymethylether; 2-methoxyethoxymethyl (MEM); or trimethylsilyl.

19. A compound of any of formulas (IV) to (VII):

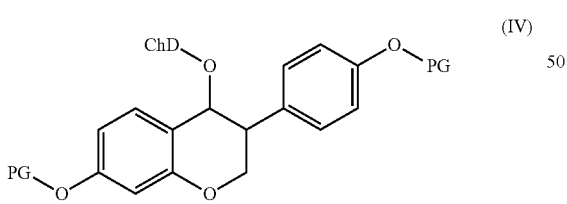

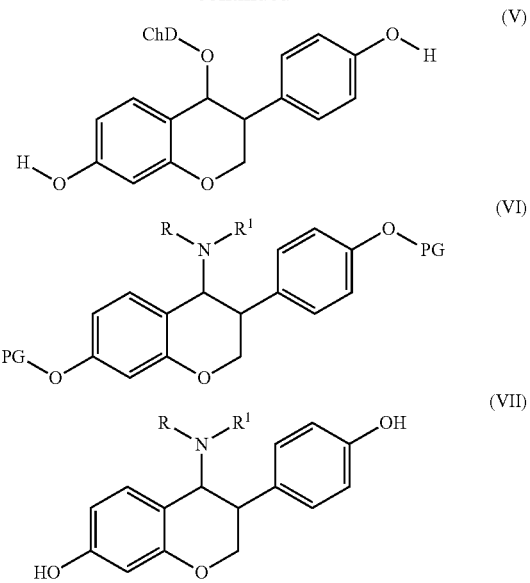

wherein
- PG is a protective group selected from acyl having 1 to 10 carbon atoms; alkoxycarbonyl wherein the alkoxy group has 1 to 10 carbon atoms; alkyl having 1 to 10 carbon atoms; a cyclic group comprising 1 to 20 carbon atoms; an ether group having 1 to 10 carbon atoms; a diol toluenesulfonyl (tosyl); or silyl,
- ChD is a chiral group having 8 to 30 carbon atoms, which has a chiral carbon atom, optionally 1 to 8 heteroatoms; and 1 to 5 rings, and
- residue $RNR^1$ is a cyclic amine having 5 to 20 carbon atoms or a non-cyclic dialkylamine, wherein each alkyl group has 1 to 20 carbon atoms, wherein the cyclic amine may comprise one or more heteroatoms.

20. A compound of claim 19, wherein
- PG is a protective group selected from acetyl; alkoxycarbonyl wherein the alkoxy group has 1 to 5 carbon atoms; methyl, ethyl, propyl or tert-butyl; tetrahydrofuran, cyclic alkyl having 5 to 10 carbon atoms, benzyl or benzoyl; methoxymethyl (MOM) or 2-methoxyethoxymethyl (MEM); a 1,2- or 1,3-diol, having 2 to 10 carbon atoms; or trimethylsilyl,
- ChD is a chiral group having 1 to 8 heteroatoms selected from O, N, or S; and/or the chiral group is linked to the isoflavane by an ester bond, and
- residue $RNR^1$ is a cyclic amine having 5 to 20 carbon atoms or a non-cyclic dialkylamine, wherein each alkyl group has 1 to 20 carbon atoms, wherein the cyclic amine comprises 1 to 5 heteroatoms.

* * * * *